US006157661A

United States Patent [19]

Walker et al.

[11] Patent Number: 6,157,661

[45] Date of Patent: Dec. 5, 2000

[54] SYSTEM FOR PRODUCING A PULSED, VARIED AND MODULATED LASER OUTPUT

[75] Inventors: Bruce R. Walker, West Jordan; Kevin D. Ostler, Riverton, both of Utah

[73] Assignee: LaserPhysics, Inc., South Jordan, Utah

[21] Appl. No.: 09/310,906

[22] Filed: May 12, 1999

[51] Int. Cl.[7] .......... H01S 3/00

[52] U.S. Cl. .......... 372/38

[58] Field of Search .......... 372/38

[56] References Cited

U.S. PATENT DOCUMENTS

| | | | |
|---|---|---|---|
| 31,279 | 6/1983 | Mefferd et al. | 372/107 |
| 34,196 | 3/1993 | Munro | 433/215 |
| 3,605,039 | 9/1971 | Harris et al. | 331/94.5 |
| 3,763,442 | 10/1973 | McMahan | 331/94.5 |
| 3,801,202 | 4/1974 | Breaux | 356/85 |
| 3,931,589 | 1/1976 | Aisenberg et al. | 331/94.5 |
| 3,943,046 | 3/1976 | De Sorga et al. | 204/159.23 |
| 3,962,656 | 6/1976 | Peressini | 331/94.5 PE |
| 3,967,214 | 6/1976 | Thatcher | 331/94.5 |
| 3,970,962 | 7/1976 | Peressini et al. | 331/94.5 PE |
| 4,007,430 | 2/1977 | Fletcher et al. | 331/94.5 D |
| 4,053,845 | 10/1977 | Gould | 330/4.3 |
| 4,061,986 | 12/1977 | Barker | 331/94.5 |
| 4,161,436 | 6/1979 | Gould | 204/151.1 R |
| 4,191,622 | 3/1980 | Phillips et al. | 204/159.22 |
| 4,203,080 | 5/1980 | Wright et al. | 331/94.5 D |
| 4,224,525 | 9/1980 | Phillips et al. | 250/531 |
| 4,280,536 | 7/1981 | Dumond et al. | 372/82 |
| 4,298,005 | 11/1981 | Mutzhas | 128/396 |
| 4,329,421 | 5/1982 | Wisnosky et al. | 430/322 |
| 4,411,931 | 10/1983 | Duong | 427/54.1 |
| 4,447,151 | 5/1984 | McLellan et al. | 356/218 |
| 4,477,901 | 10/1984 | McMahan | 372/64 |
| 4,479,225 | 10/1984 | Mohler et al. | 372/97 |
| 4,522,593 | 6/1985 | Fischer | 433/136 |
| 4,551,100 | 11/1985 | Fischer | 433/218 |
| 4,573,159 | 2/1986 | Aagano et al. | 372/34 |
| 4,578,055 | 3/1986 | Fischer | 604/2 |
| 4,582,701 | 4/1986 | Piechota, Jr. | 424/52 |
| 4,611,327 | 9/1986 | Clark et al. | 372/58 |
| 4,613,972 | 9/1986 | Bettman | 372/101 |
| 4,615,033 | 9/1986 | Nakano et al. | 372/99 |
| 4,615,034 | 9/1986 | von Gunten et al. | 372/99 |
| 4,625,317 | 11/1986 | Kolb et al. | 372/88 |
| 4,635,272 | 1/1987 | Kamide et al. | 372/87 |
| 4,656,635 | 4/1987 | Baer et al. | 372/27 |
| 4,661,070 | 4/1987 | Friedman | 433/203.1 |
| 4,665,524 | 5/1987 | Cotter | 372/18 |
| 4,674,092 | 6/1987 | Cannon | 372/33 |
| 4,687,663 | 8/1987 | Schaeffer | 424/52 |
| 4,696,010 | 9/1987 | Eastman | 372/34 |
| 4,697,269 | 9/1987 | Ohara | 372/34 |
| 4,698,835 | 10/1987 | Ono et al. | 378/136 |
| 4,704,583 | 11/1987 | Gould | 330/4.3 |
| 4,713,825 | 12/1987 | Adsett | 372/107 |
| 4,716,569 | 12/1987 | Bees | 372/38 |
| 4,723,257 | 2/1988 | Baer et al. | 372/108 |
| 4,727,554 | 2/1988 | Watanabe | 372/36 |
| 4,769,824 | 9/1988 | Seki | 372/107 |
| 4,784,135 | 11/1988 | Blum et al. | 128/303.1 |
| 4,817,096 | 3/1989 | Nighan et al. | 372/5 |
| 4,862,469 | 8/1989 | Couillaud et al. | 372/33 |
| 4,872,936 | 10/1989 | Engelbrecht | 156/307 |
| 4,877,401 | 10/1989 | Higuchi et al. | 433/215 |
| 4,887,271 | 12/1989 | Taylor | 372/29 |
| 4,895,517 | 1/1990 | Fischer | 433/224 |
| 4,896,330 | 1/1990 | Krueger et al. | 372/65 |
| 4,904,872 | 2/1990 | Grix et al. | 250/423 |

(List continued on next page.)

*Primary Examiner*—Frank G. Font
*Assistant Examiner*—Armando Rodriguez
*Attorney, Agent, or Firm*—Daniel McCarthy

[57] ABSTRACT

A system and method are disclosed for providing a laser beam that is varied, such as being pulsed or modulated, rather than being a laser beam of constant intensity. Specific circuitry that includes timing and triggering means for pulsing a laser beam is disclosed, and methods and software for modulating a laser beam are disclosed. Pulsed and modulated laser beams have wide variety of applications, including curing polymeric materials such as dental composites. Modulated light from sources other than lasers may also be used for such curing.

23 Claims, 22 Drawing Sheets

U.S. PATENT DOCUMENTS

| | | | |
|---|---|---|---|
| 4,941,873 | 7/1990 | Fisher | 604/54 |
| 4,968,251 | 11/1990 | Darnell | 433/216 |
| 4,971,556 | 11/1990 | Ritano | 433/102 |
| 4,983,380 | 1/1991 | Yarborough | 424/52 |
| 4,983,381 | 1/1991 | Torres Zaragoza | 424/53 |
| 4,989,217 | 1/1991 | Ostler | 372/107 |
| 4,990,089 | 2/1991 | Munro | 433/215 |
| 4,995,540 | 2/1991 | Collin et al. | 222/132 |
| 5,002,854 | 3/1991 | Fan et al. | 430/270 |
| 5,002,855 | 3/1991 | Fan et al. | 430/270 |
| 5,005,181 | 4/1991 | Yoshioka et al. | 372/59 |
| 5,007,737 | 4/1991 | Hirleman, Jr. | 356/336 |
| 5,007,837 | 4/1991 | Werly | 433/226 |
| 5,009,885 | 4/1991 | Yarborough | 424/53 |
| 5,031,768 | 7/1991 | Fischer | 206/370 |
| 5,032,178 | 7/1991 | Cornell | 106/35 |
| 5,033,650 | 7/1991 | Colin et al. | 222/137 |
| 5,040,182 | 8/1991 | Spinelli et al. | 372/18 |
| 5,041,280 | 8/1991 | Smigel | 424/52 |
| 5,055,743 | 10/1991 | Ekstrand | 315/111.51 |
| 5,098,299 | 3/1992 | Fischer | 433/215 |
| 5,098,303 | 3/1992 | Fischer | 433/215 |
| 5,123,845 | 6/1992 | Vassiliadis et al. | 433/215 |
| 5,127,730 | 7/1992 | Breije et al. | 356/318 |
| 5,149,659 | 9/1992 | Hakuta et al. | 666/691 |
| 5,154,861 | 10/1992 | McBrierty et al. | 264/1.4 |
| 5,175,077 | 12/1992 | Grossa | 430/327 |
| 5,181,214 | 1/1993 | Berger et al. | 372/34 |
| 5,181,215 | 1/1993 | Sam et al. | 372/34 |
| 5,214,658 | 5/1993 | Ostler | 372/23 |
| 5,238,744 | 8/1993 | Williams et al. | 428/412 |
| 5,246,371 | 9/1993 | Fischer | 433/217 |
| 5,254,114 | 10/1993 | Reed, Jr. et al. | 606/15 |
| 5,269,684 | 12/1993 | Fischer | 433/90 |
| 5,275,564 | 1/1994 | Vassiliadis et al. | 433/226 |
| 5,280,536 | 1/1994 | Dumond et al. | 372/82 |
| 5,286,257 | 2/1994 | Fischer | 604/82 |
| 5,289,919 | 3/1994 | Fischer | 604/218 |
| 5,306,143 | 4/1994 | Levy | 433/29 |
| 5,318,562 | 6/1994 | Levy et al. | 606/16 |
| 5,321,715 | 6/1994 | Trost | 372/69 |
| 5,324,200 | 6/1994 | Vassiliadis et al. | 433/224 |
| 5,328,462 | 7/1994 | Fischer | 604/82 |
| 5,332,092 | 7/1994 | Fischer | 206/365 |
| 5,349,591 | 9/1994 | Weston et al. | 372/25 |
| 5,356,291 | 10/1994 | Darnell | 433/216 |
| 5,360,834 | 11/1994 | Popall et al. | 522/36 |
| 5,364,267 | 11/1994 | Fischer | 433/26 |
| 5,376,006 | 12/1994 | Fisher | 433/215 |
| 5,387,103 | 2/1995 | Fischer | 433/89 |
| 5,409,631 | 4/1995 | Fisher | 252/186.5 |
| 5,425,641 | 1/1995 | Fischer | 433/226 |
| 5,425,953 | 6/1995 | Sintov et al. | 424/404 |
| 5,445,523 | 8/1995 | Fischer et al. | 433/90 |
| 5,464,348 | 11/1995 | Fischer et al. | 433/26 |
| 5,467,362 | 11/1995 | Mrrray | 372/5 |
| 5,472,991 | 12/1995 | Schmitt | 522/4 |
| 5,478,235 | 12/1995 | Schuldt et al. | 433/37 |
| 5,501,579 | 3/1996 | Kimura et al. | 417/269 |
| 5,501,599 | 3/1996 | Rechmann | 433/215 |
| 5,534,562 | 7/1996 | Jensen et al. | 523/118 |
| 5,550,853 | 8/1996 | Ostler | 372/34 |
| 5,558,230 | 9/1996 | Fischer et al. | 226/570 |
| 5,575,655 | 11/1996 | Darnell | 433/216 |
| 5,603,701 | 2/1997 | Fischer | 604/211 |
| 5,611,687 | 3/1997 | Wagner | 433/80 |
| 5,618,273 | 4/1997 | Fischer | 604/211 |
| 5,632,739 | 5/1997 | Anderson et al. | 606/2 |
| 5,635,162 | 6/1997 | Fischer | 424/49 |
| 5,643,206 | 7/1997 | Fischer | 604/82 |
| 5,645,428 | 7/1997 | Yarborough | 433/215 |
| 5,665,066 | 9/1997 | Fischer | 604/82 |
| 5,667,386 | 9/1997 | Black et al. | 433/213 |
| 5,685,712 | 11/1997 | Fischer | 433/26 |
| 5,692,900 | 12/1997 | Fischer | 433/26 |
| 5,697,903 | 12/1997 | Fischer | 604/82 |
| 5,697,918 | 12/1997 | Fischer et al. | 604/227 |
| 5,700,148 | 12/1997 | Fischer et al. | 433/217.1 |
| 5,708,052 | 1/1998 | Fischer et al. | 523/116 |
| 5,722,829 | 3/1998 | Wilcox et al. | 433/90 |
| 5,722,833 | 3/1998 | Fischer et al. | 433/217.1 |
| 5,725,843 | 3/1998 | Fischer | 424/49 |
| 5,746,598 | 5/1998 | Fischer | 433/216 |
| 5,766,011 | 6/1998 | Sibner | 433/215 |
| 5,770,105 | 6/1998 | Fischer | 252/186.25 |
| 5,770,182 | 6/1998 | Fischer | 424/49 |
| 5,775,904 | 7/1998 | Riltano | 433/102 |
| 5,776,127 | 7/1998 | Anderson et al. | 606/2 |
| 5,785,955 | 7/1998 | Fischer | 424/49 |
| 5,800,163 | 9/1998 | Rueggeberg et al. | 433/9 |
| 5,803,734 | 9/1998 | Knutson | 433/139 |
| 5,816,804 | 10/1998 | Fischer | 433/90 |
| 5,846,058 | 12/1998 | Fischer | 433/216 |
| 5,851,512 | 12/1998 | Fischer | 424/49 |
| 5,855,870 | 1/1999 | Fischer | 424/49 |
| 5,858,332 | 1/1999 | Jensen et al. | 424/53 |
| 5,860,806 | 1/1999 | Pranitis, Jr. et al. | 433/80 |
| 5,868,769 | 2/1999 | Rosenblood et al. | 606/161 |
| 5,882,201 | 3/1999 | Salem | 443/216 |
| 5,890,900 | 4/1999 | Fischer et al. | 433/149 |
| 5,890,901 | 4/1999 | Fischer et al. | 433/149 |
| 5,922,307 | 7/1999 | Montgomery | 424/53 |
| 5,947,278 | 9/1999 | Sawhney et al. | 206/216 |
| 5,967,778 | 10/1999 | Riltano | 433/77 |
| 5,985,249 | 11/1999 | Fischer | 424/49 |
| 6,008,264 | 12/1999 | Ostleret al | 522/4 |

LASER TUBE
CATHODE
ANODE
IN 1
IN 2
IN 3
IN 4
3-2-1
3-2-2
3-3-1
3-5-1
Primary
Sec 1
Sec 2
Sec 3
Sec 4
UC3825N 512
-IN
+IN
E/A OUT
CLK
Rt
Ct
RAMP
SFT STRT
ILim
GND
OUT A
PWR GND
Vc
OUT B
Vcc
SW REF
+12V
+12V
500
501
502
503
504
505
506
507
508
509
510
511
513
514
515
516
517
518
519
520
521
522
524
525
526
527
528
529
530
531
532
533
534
535
536
537
538
539
540
541
542
543
544
545

OUT 1
OUT 2
3-3-2
3-5-1
600
+12V
-12V
+15V
601
602
603
604
605
606
607
608
609
610
611
612
613
614
615
616
617
618
619
620
621
622
623
624
625
626
628
629
630
631
632
633
634
635
636
637
638
639
640

SYSTEM FOR PRODUCING A PULSED, VARIED AND MODULATED LASER OUTPUT

BACKGROUND OF THE INVENTION

A. Field of the Invention

This invention relates to the lasers which produce pulsed, modulated or varied laser light output and methods for producing pulsed, modulated and varied laser light output.

B. The Background Art

In the prior art, lasers typically provided a continuous laser beam output of a particular wavelength and power. While it may take a short period of time for a prior art laser to power up and provide the expected power output, once in use, the laser provided a continuous beam of a predetermined wavelength and power intensity.

In many applications, it is not necessary to provide a continuous laser output of a particular power level. Some applications, such as curing polymeric materials, will be served as well or even better if the laser beam is not continuously on. Further, by not keeping the laser beam continuously on, the load on the laser is less and a smaller, less expensive laser unit may be produced to perform the function once performed by a larger, higher load and more expensive unit.

Representative examples of prior art lasers are shown in U.S. Pat. Nos. 5,550,853; 5,214,658; 4,447,151; 5,280,536 and 4,989,217, each of which is hereby incorporated by reference.

In the field of polymer curing, whether for dental or other uses, when lasers or other light sources were used for curing purposes, typically a constant light beam or laser beam of a desired wavelength was used.

SUMMARY OF THE INVENTION

It is an object of some preferred embodiments of the invention to produce a varied laser output. It is a feature of some preferred embodiments of the invention that laser output may be pulsed or modulated through hardware or software control.

It is an object of some embodiments of the invention to produce pulsed lasing energy. It is a feature of some embodiments of the invention that hardware circuitry is provided that creates a pulsed laser output.

It is an object of some embodiments of the invention to produce a pulsed laser output using circuitry that is minimized for cost efficiency, power efficiency and size. The preferred circuitry achieves that.

It is an object of some embodiments of the invention to provide a laser with peak pulses and peak light output that is much higher than a continuous wave laser of the same power and load capabilities. It is a feature of some embodiments of the invention that a laser is provided which uses a low average power and minimized circuitry but which utilized AC line pulses to produce higher peak laser pulses than a continuous beam laser would.

It is an object of some embodiments of the invention to provide a laser that has a higher peak power output than continuous beam lasers of similar size and cost characteristics. Some of preferred circuitry uses AC line pulses to do this.

It is an object of some preferred embodiments of the invention to reduce the parts count in a laser configuration for curing polymers. By taking advantage of AC line characteristics, efficiently utilizing power input, and varying the laser beam output, a small and inexpensive laser is produced that has the same performance capabilities of larger and more expensive prior art continuous beam lasers.

It is an object of some embodiments of the invention to provide a varied laser output that may be used for a variety of commercial, industrial, medical and dental applications.

It is an object of some embodiments of the invention to provide a varied laser output that may be used for the curing of polymer composites.

It is an object of the invention to provide a laser system that is smaller, less expensive and more efficient than prior art laser systems that would be required to perform the same task. This is achieved by running the laser between peak modes, but turning off the laser when efficiency drops too low, resulting in a pulsed output. Such a laser could be applied to composite curing (for dental or other uses), drilling, cutting, holographic imaging, sterilization, interferometry, distance measuring, spectroscropy, and any other use where a continuous laser beam is not required.

It is an object of some embodiments of the invention to provide a varied laser output that is useful for curing dental composites. In the field of dentistry, there is a significant trend away from the use of metal materials for repair and reconstruction of teeth and the construction of dental appliances. Dentists and dental technicians are now relying on polymeric materials for applications which in the past required the use of metals. Polymeric materials are preferred by many dentists due to their ease of formation, superior aesthetic results, and avoidance of concerns about release of mercury from amalgams used in other dental restorative materials.

Polymeric dental materials can be very durable if prepared and cured properly. In particular, the polymerization process that the materials undergo should be tailored to provide a hard and durable resulting dental appliance or reconstruction, but should not exhibit brittleness, stress cracking, shrinkage or other undesirable qualities. The particular application of a dental material requires that it has physical characteristics tailored to that application in order to maximize performance.

It is an object of some embodiments of the invention to provide a method and system for curing polymeric dental materials. It is a feature of a preferred embodiment of the invention that various lasers are used to cure polymeric dental materials. It is a consequent advantage of the invention that the dental materials may be cured quickly and to a predetermined physical state.

It is an object of some preferred embodiments of the invention to provide a method and system for tailoring the post-cure properties of dental materials. It is a feature of the invention that light is applied to the dental materials to cause their polymerization and cure.

It is an object of some preferred embodiments of the invention to tailor the post cure properties of dental materials. It is a feature of the invention that light is applied to the dental materials according to various power, wave form and modulation parameters in order to cause the particular dental materials to cure into a final form with desired properties. It is a consequent advantage of the invention that the performance of the dental materials may be optimized for a particular application or environment by curing techniques.

It is an object of some preferred embodiments of the invention to utilize a light power source in order to cure dental materials on an intermittent or sporadic basis so that a single light power source may serially provide power to several physically discrete quantums of dental materials to be cured. It is a feature of the invention that some preferred embodiments of the invention involve applying light to a dental material in a periodic fashion such as on/off, so that while a first dental material is experiencing the off-phase of its cure, the light power source may be used to provide light and power to the on-phase of a second dental material to be cured. It is an advantage of the invention that in a dental office having several dentists or technicians, multiple dental material curing lights could be powered for simultaneous use by a single light power source, reducing the cost of the capital investment in equipment.

It is an object of some preferred embodiments of the invention to affect the growth of polymer chains in polymeric dental materials. It is a feature of the invention that light source power modulation is employed in order to initiate and control the growth of polymer chains in polymeric dental materials so that the resulting materials have chains of a desired length, resulting a cured dental material with desired strength, hardness, lack of brittleness and other properties desired for its particular use.

It is an object of some preferred embodiments of the invention to provide a light source power modulation scheme that minimizes shrinkage of a dental material during cure. It is a feature of the invention that light may be first applied to the dental material at high power level, dropped over time to a lower power level and then maintained at the lower power level. It is an advantage of the invention that such a modulation scheme minimizes shrinkage in a dental material.

It is an object of some preferred embodiments of the invention to provide a light source power modulation scheme that creates a post-cure dental material that is flexible. It is a feature of the invention that light may be applied to the dental material at a first power level, held constant at that first power level for a period of time, and then increased over time to a second power level. It is an advantage of the invention that such a modulation scheme produces flexibility in a dental material.

It is an object of some preferred embodiments of the invention to provide a light source power modulation scheme that creates a post-cure dental material that has great surface or wear strength. It is a feature of the invention that light may be applied to the dental material at a first high power level, quickly reduced to a lower power level, and then gradually increased to about the first high power level again. It is an advantage of the invention that such a modulation scheme produces significant surface or wear strength in a dental material.

It is an object of some preferred embodiments of the invention to provide a light source power modulation scheme that creates a post-cure dental material that is useful as a pit and fissure sealant. It is a feature of the invention that light may be applied to the dental material at a first high power level, decreased to a second lower power level, and then held constant at about that second power level for a period of time. It is an advantage of the invention that such a modulation scheme produces a dental material that has the qualities needed to serve as a pit and fissure sealant.

It is an object of some preferred embodiments of the invention to provide a light source power modulation scheme that creates a post-cure dental material that is useful as a bonding agent for indirect applications. It is a feature of the invention that light may be applied to the dental material in an increasing and decreasing pattern according to a sine wave, particularly initiating light exposure at a mid-power level on the sine wave. It is an advantage of the invention that such a modulation scheme produces a dental material that has characteristics suitable for use as a bonding agent for indirect applications.

It is an object of some preferred embodiments of the invention to provide a light source power modulation scheme that creates a post-cure dental material that is useful as a bonding agent for direct applications (such as orthodontics). It is a feature of the invention that light may be applied to the dental material according to a discontinuous waveform. For example, the waveform may include initiating power and holding it constant for a period of time at a first low power level, turning power to the light source off for a period of time, and then reinitiating power and holding it constant for a period fo time at a second higher power level. It is an advantage of the invention that such a modulation scheme produces a dental material useful as a bonding agent for orthodontic applications.

Many other modulation schemes and tailoring the post-cure characteristics of the dental material or other polymeric material for almost any use are possible within the inventive concept.

The various embodiments of the invention has application not only in curing dental composites, but in curing non-dental composites such as industrial polymers and for other uses as well. The invention is not intended to be solely limited either to the field of dentistry or to the field of polymerization.

Other objects, features and advantages of the invention will become apparent to persons of ordinary skill in the art upon reading the specification and reviewing the appended figures.

BRIEF DESCRIPTION OF THE DRAWINGS

FIGS. 3-1, 3-2, 3-3, 3-4, 3-5 and 3-6 depicts circuitry used in one preferred embodiment of the invention.

FIGS. 4–16 depict various laser and light output waveforms of some preferred embodiments of the invention.

DETAILED DESCRIPTION OF THE INVENTION

A. A Preferred Hardware Environment

Figure 1:
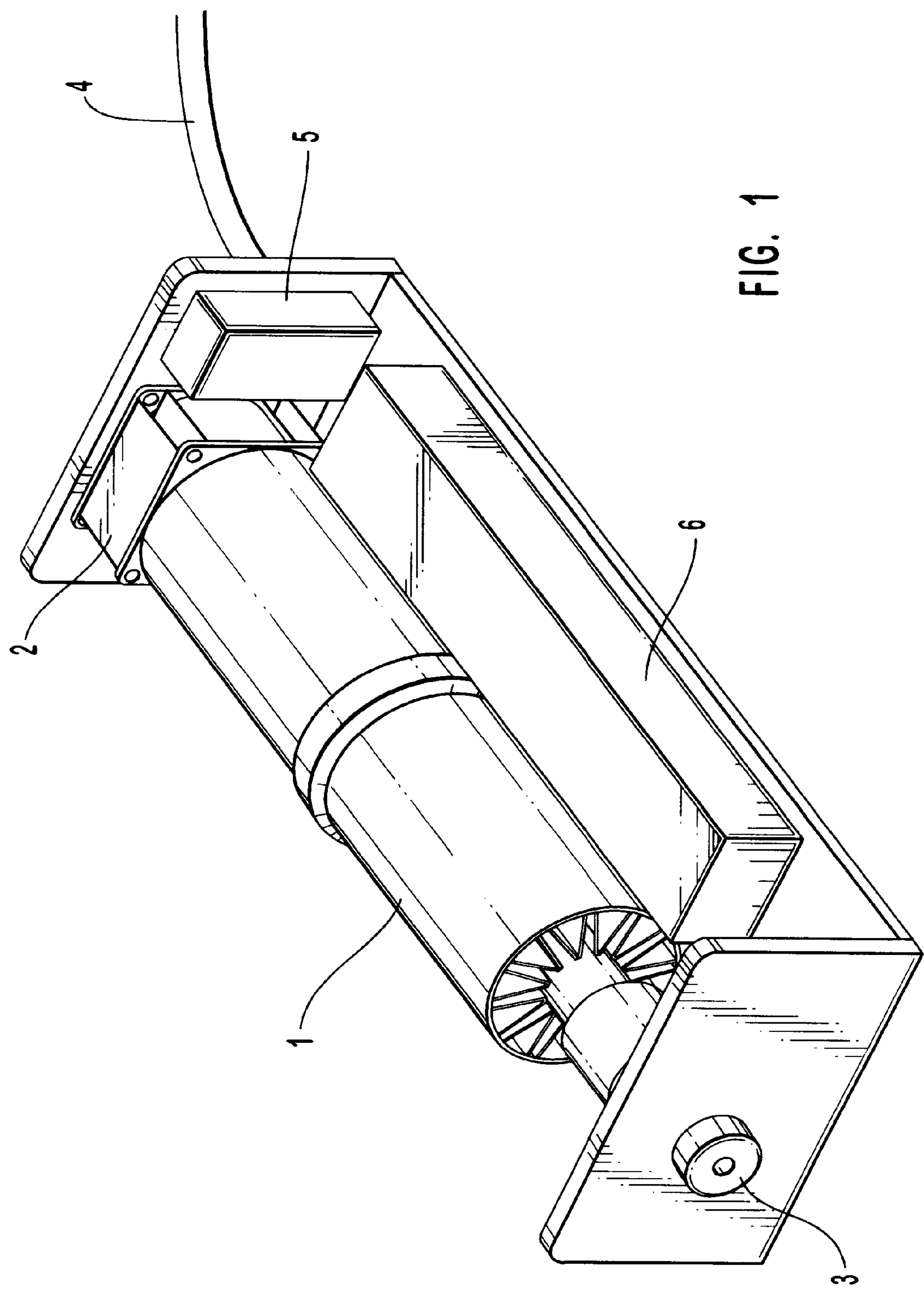
FIG. 1 depicts a laser system assembled according to one preferred embodiment of the invention.

Referring to FIG. 1, a laser of the invention is depicted. The laser includes a laser tube 1 which may is a prior art laser tube and is not the subject of this invention. The laser tube could be use any of the following gases and mixtures thereof in order to produce laser light of a desired wavelength. In the preferred embodiment an argon laser tube is used, but any other laser could be used as well. At the rear end of the laser tube 1 is a laser tube cooling fan 2 that serves to keep the laser tube 1 from overheating. At the front of the laser tube 1 is a laser output coupler 3 from which laser light is emitted. The laser output coupler 3 may be attached to any desired laser light delivery apparatus in order to guide the laser light to a desired final destination. A power cord 4 provides electrical power for operation of the laser, and a circuit breaker and key switch 5 are provided for safety. A process control board 6 is provided with circuitry and logic that controls operation of the laser in order to produce a pulsed, modulated or varied laser output. The process control board 6 is intended to be representative of both hardware and/or software that can be used in conjunction with a laser tube to produce a desired laser output by varying power, frequency, ramp-up, ramp-down, timing and other factors. FIGS. 2, 3-1, 3-2, 3-3, 3-4, 3-5 and 3-6 depict hardware that could be used to cause a laser to provide a desired varied, modulated or pulsed laser output, and later in this document, sample computer source code is provided that can be used to provide varied laser output.

For the purposes of this document, a "varied" laser output is any laser output that is varied from or departs from a continuous laser beam, except during power up and except from power line noise, static or fluctuations. For the purposes of this document, a "pulsed" laser output is one in which the output is formed by a series of laser pulses, in which each discrete laser pulse delivers a specific quantity of energy and in which each discrete laser pulse is followed by a period of time in which there is no laser energy delivered. For the purposes of this document, a "modulated" laser output is one in which the laser energy is modulated or varied over time in a controlled manner.

Figure 2:
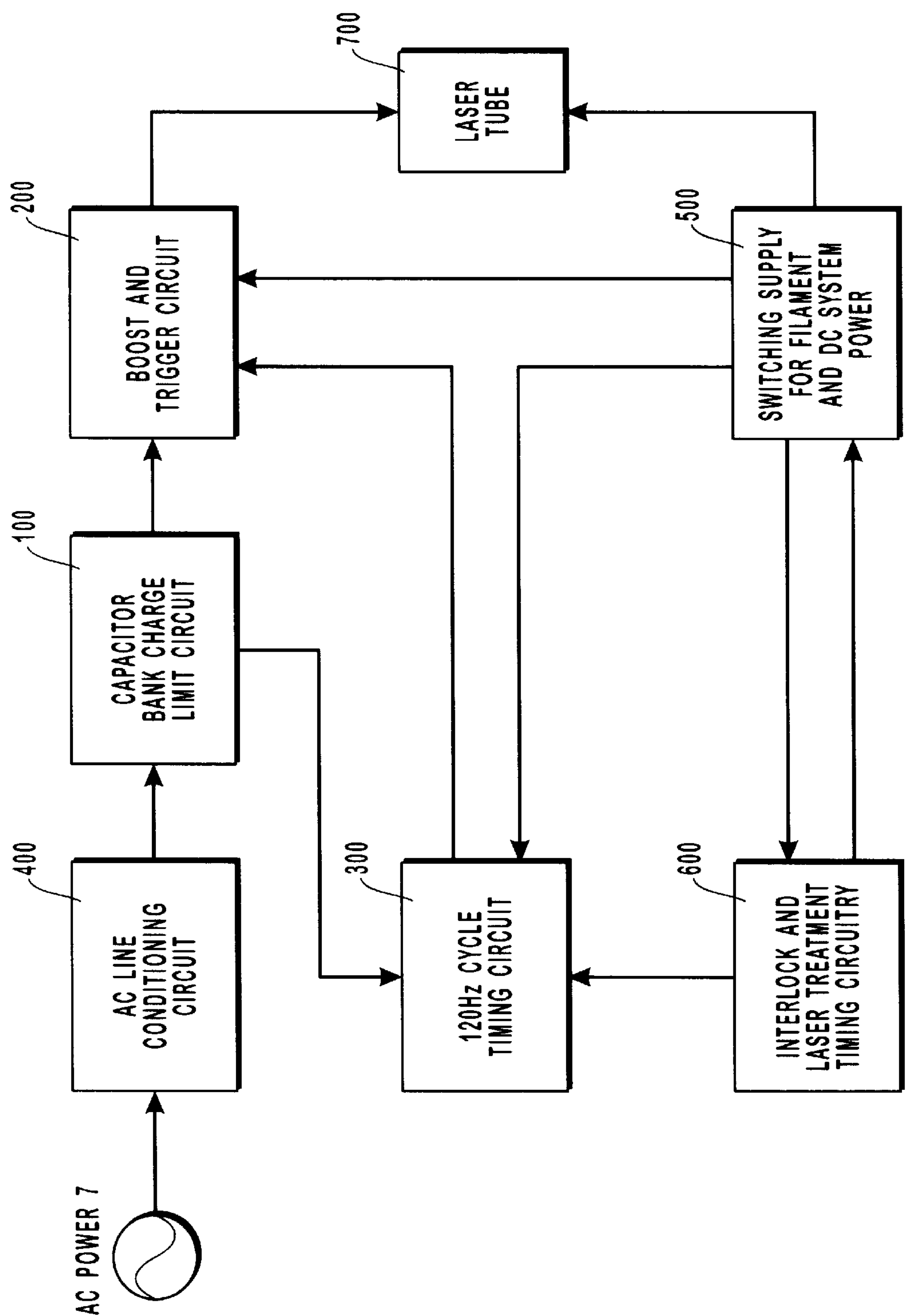
FIG. 2 depicts a block diagram representative of various hardware components used in one preferred embodiment of the invention.

Referring to FIG. 2, a block diagram of one preferred embodiment of circuitry that provides a varied laser output according to the invention is shown. AC power line 7 supplies AC power for laser operation. The AC power flows to an AC line conditioning circuit 400 which is included in the preferred embodiment of the invention but which is optional. The AC line conditioning circuit 400 protects the laser and laser control circuitry from transient surges on AC power lines. It also attenuates electromagnetic noise generated by the laser system in order to minimize the amount of noise placed on the AC power lines by the system. Clean power from the AC line conditioning circuit 400 is provided both to the capacitor bank charge limit circuit 100 and to the 120 Hz cycle timing circuit 300.

The capacitor bank charge limit circuit 100 uses a capacitor, which is allowed to charge to a predetermined voltage, in order to deliver a consistent current to the laser tube 700. The 120 Hz cycle timing circuit 300 performs a timing function in order to produce a desired varied laser output. In the preferred embodiment of the invention described in greater detail below, the 120 Hz cycle timing circuit times a pulsed laser output from 1 millisecond to 4 milliseconds in duration which occurs every full wave-rectified cycle (120 times per second when operating from 60 Hz line power). The timing provided by the timing circuit 300 could be any desired timing in other embodiments of the invention.

Boost and trigger circuit 200 boosts voltage in the system and provides a readily repeatable trigger pulse in order to ensure reliable laser tube starting. A switching supply for filament and system DC power 500 is optional but is provided in the preferred embodiment of the invention. In the preferred embodiment described in greater detail below, the switching supply 500 supplies power for non-isolated low voltage power to drive the filament, it supplies isolated +15 volt DC power to drive the laser tube cooling fan and for the key-switch interlock and optional system foot-switch and hand switch inputs, and it supplies non-isolated ±12 volts DC power to process control board electronics. In the preferred embodiment of the invention, interlock and laser treatment timer circuitry 600 is provided that provides isolated user interfaces such as a key-switch interlock, foot switch input and 1 and 2 second laser treatment time selection inputs. It also provides several different laser treatment timing options such as 1, 2 and 3 second treatment times with a minimum of 1, 2 or 3 seconds of off time, respectively, between each treatment. In alternative embodiments of the invention, some of these functions could be omitted, the values could be changed, and additional functions could be added.

Referring now to FIGS. 3-1, 3-2, 3-3, 3-4, 3-5 and 3-6, a circuit diagrams of one preferred embodiment of the invention is depicted. These diagrams provide detail of the preferred implementation of the blocks from the block diagram of FIG. 2. Depicted are blocks 100 for the capacitor bank charge limit circuit, 200 for the boost and trigger circuit, 300 for the preferred 120 Hz cycle timing circuit, 400 for the AC line conditioning circuit (optional), 500 for the switching supply for filament and system DC power (optional), and 600 for interlock and laser treatment timer circuitry (optional).

Capacitor Bank Charge Limit Circuit 100

Figures 1, 3:
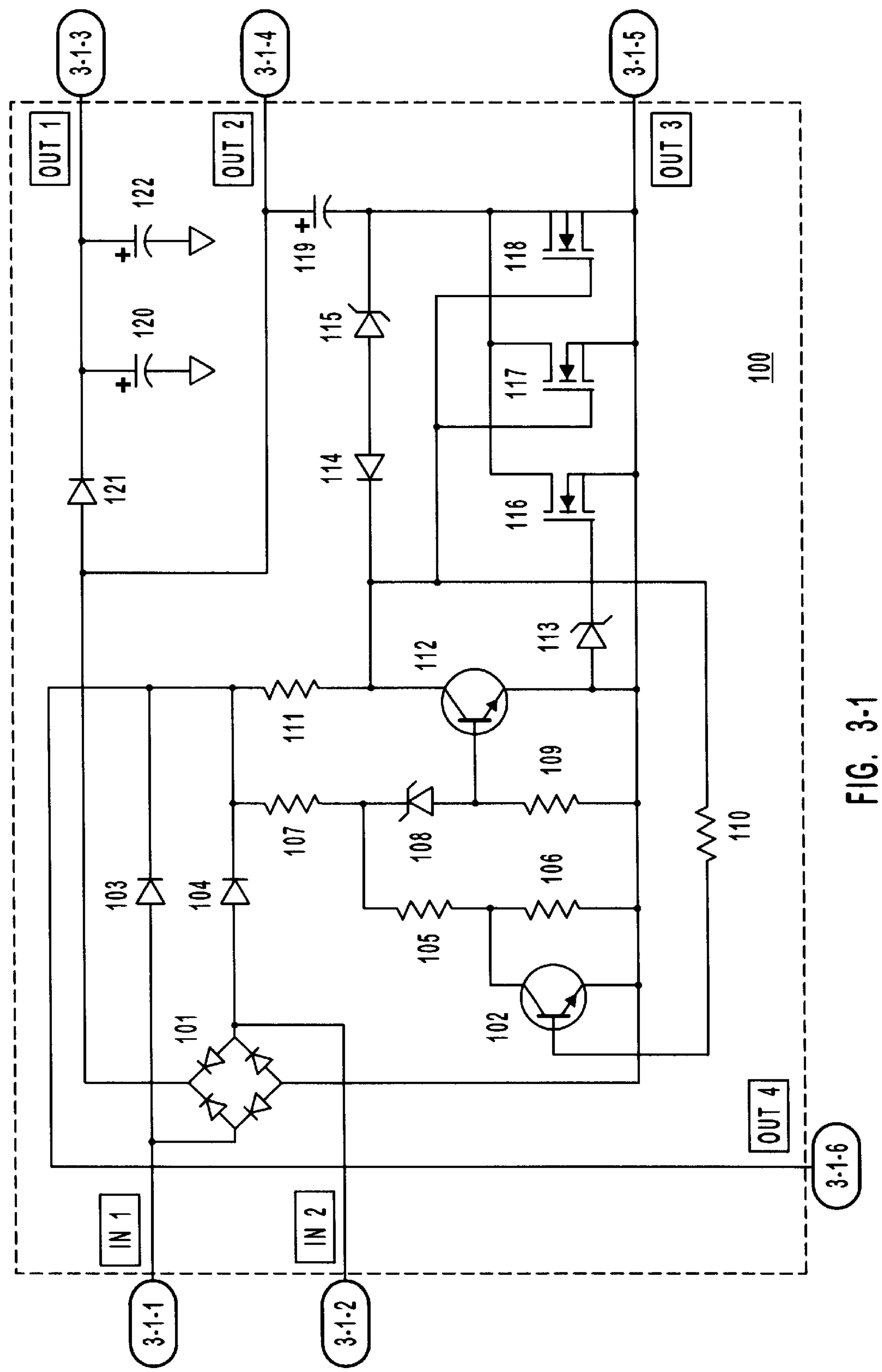
Figures 2, 3:
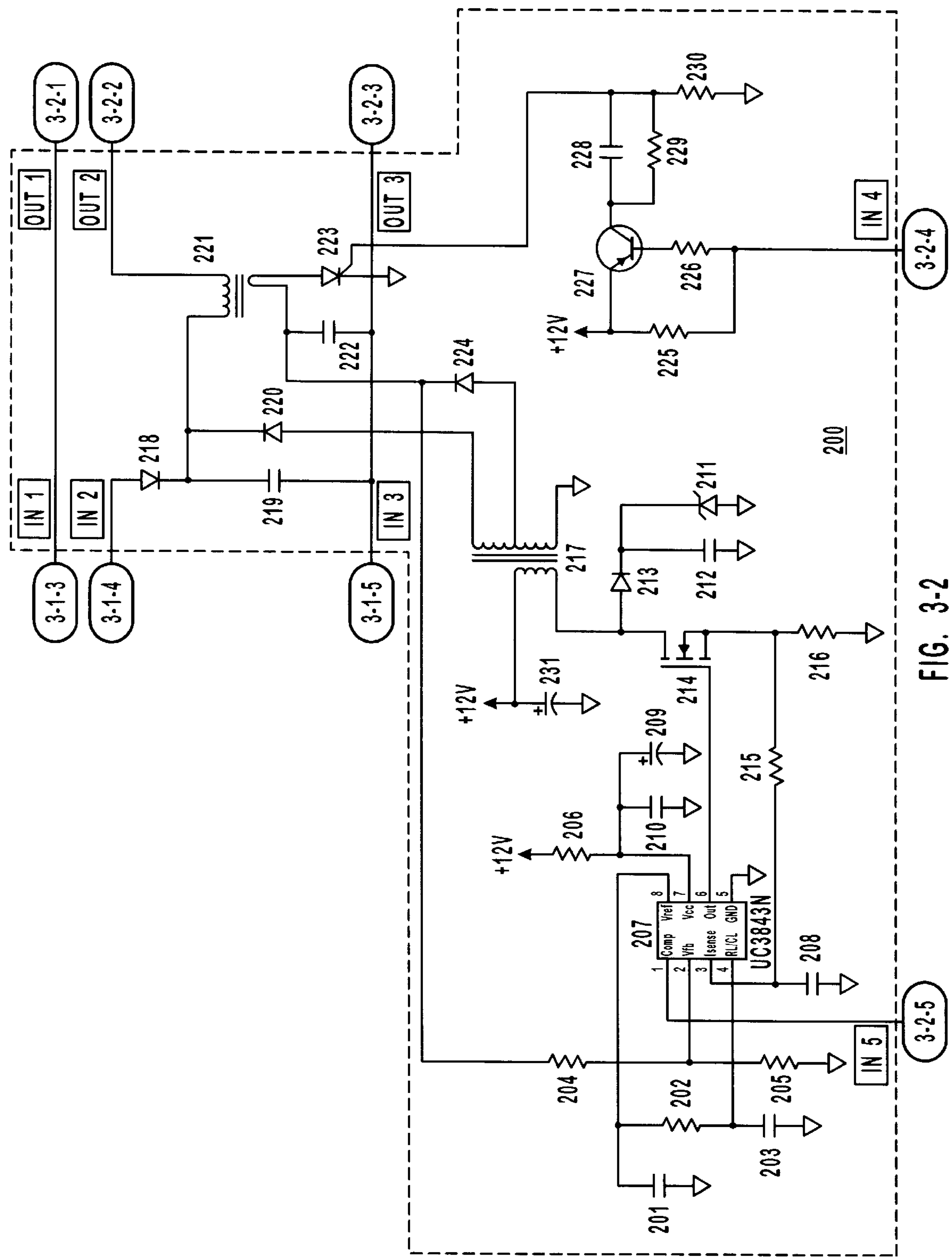
Figure 3:
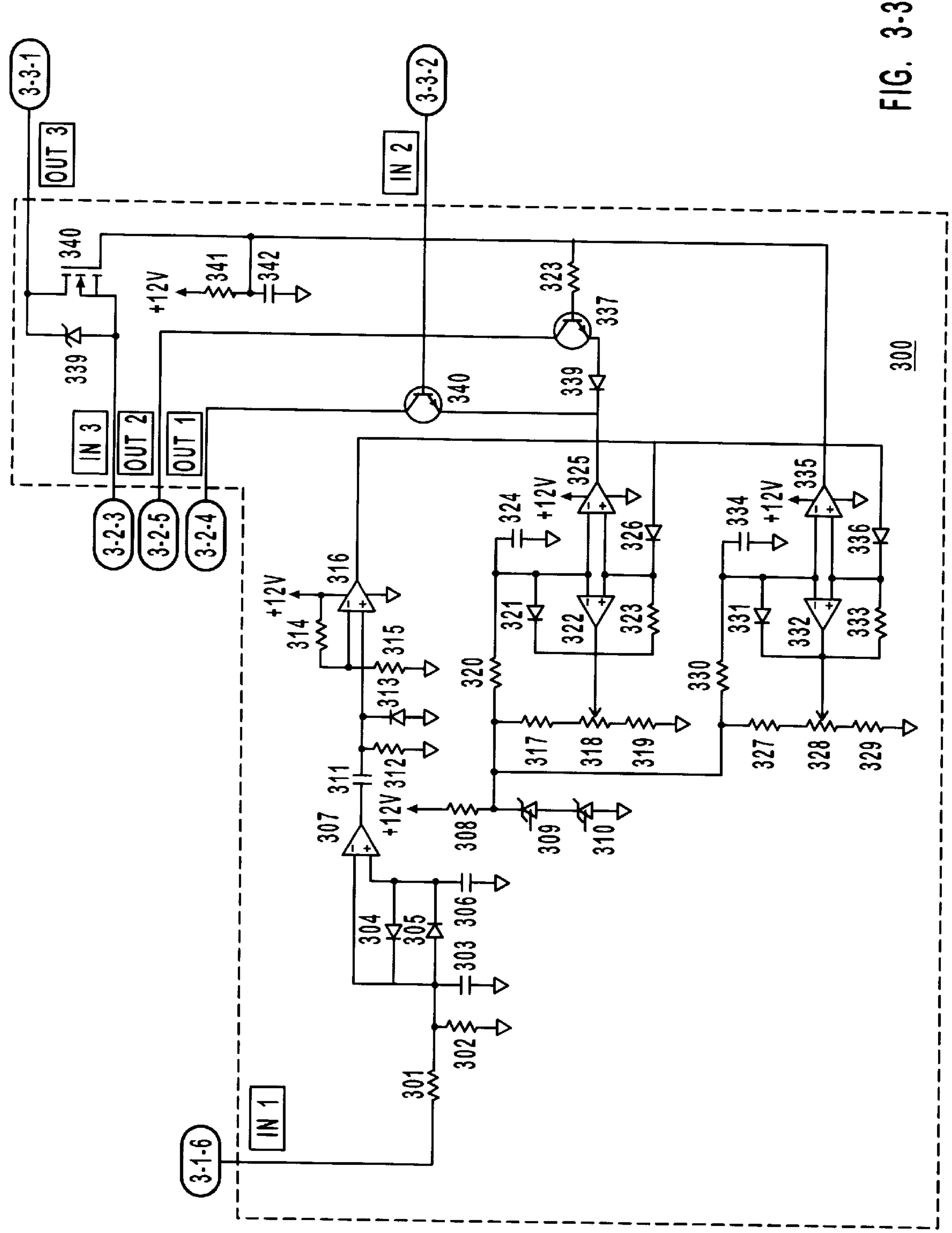
Figures 3, 4:
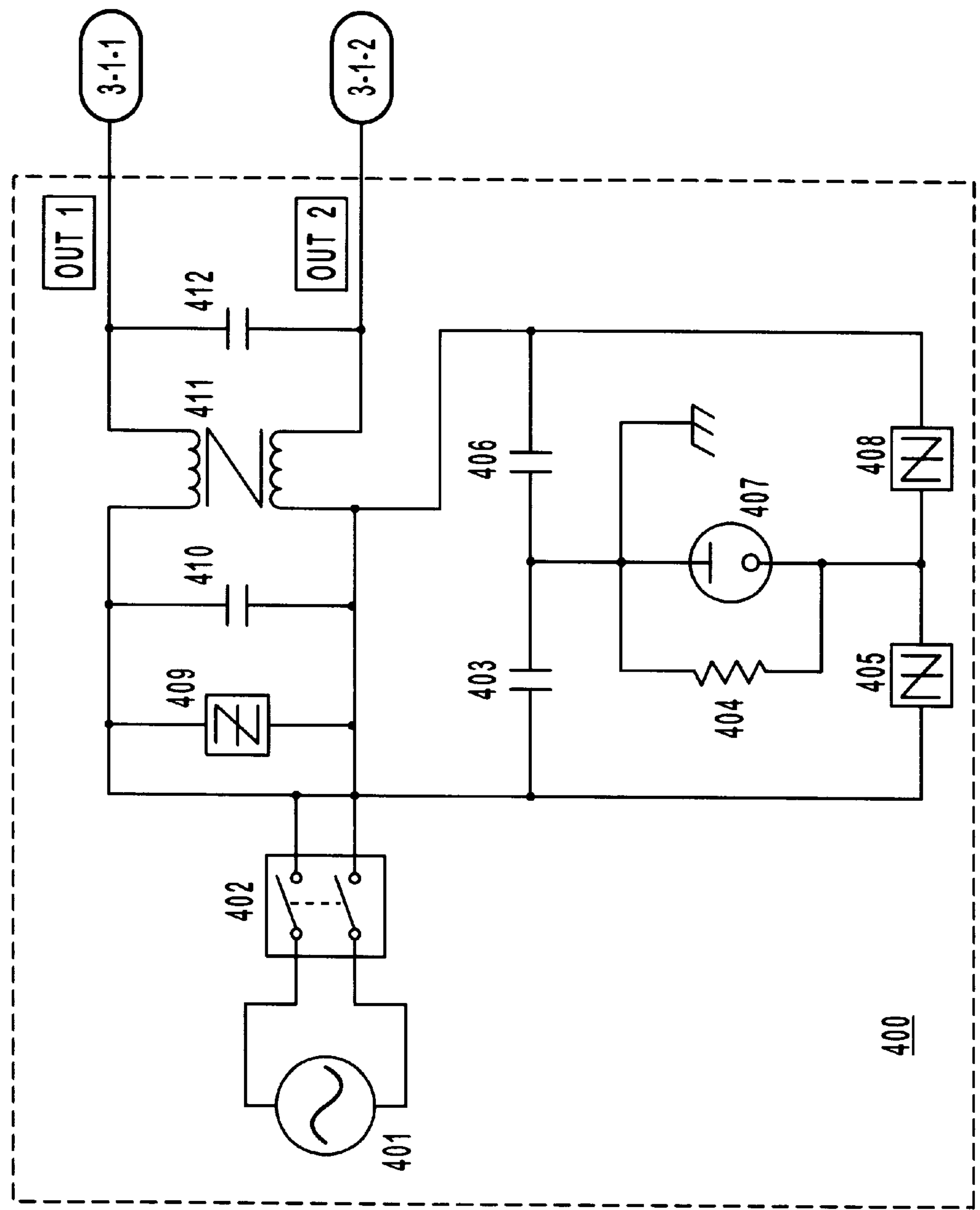
Figures 3, 4, 5:
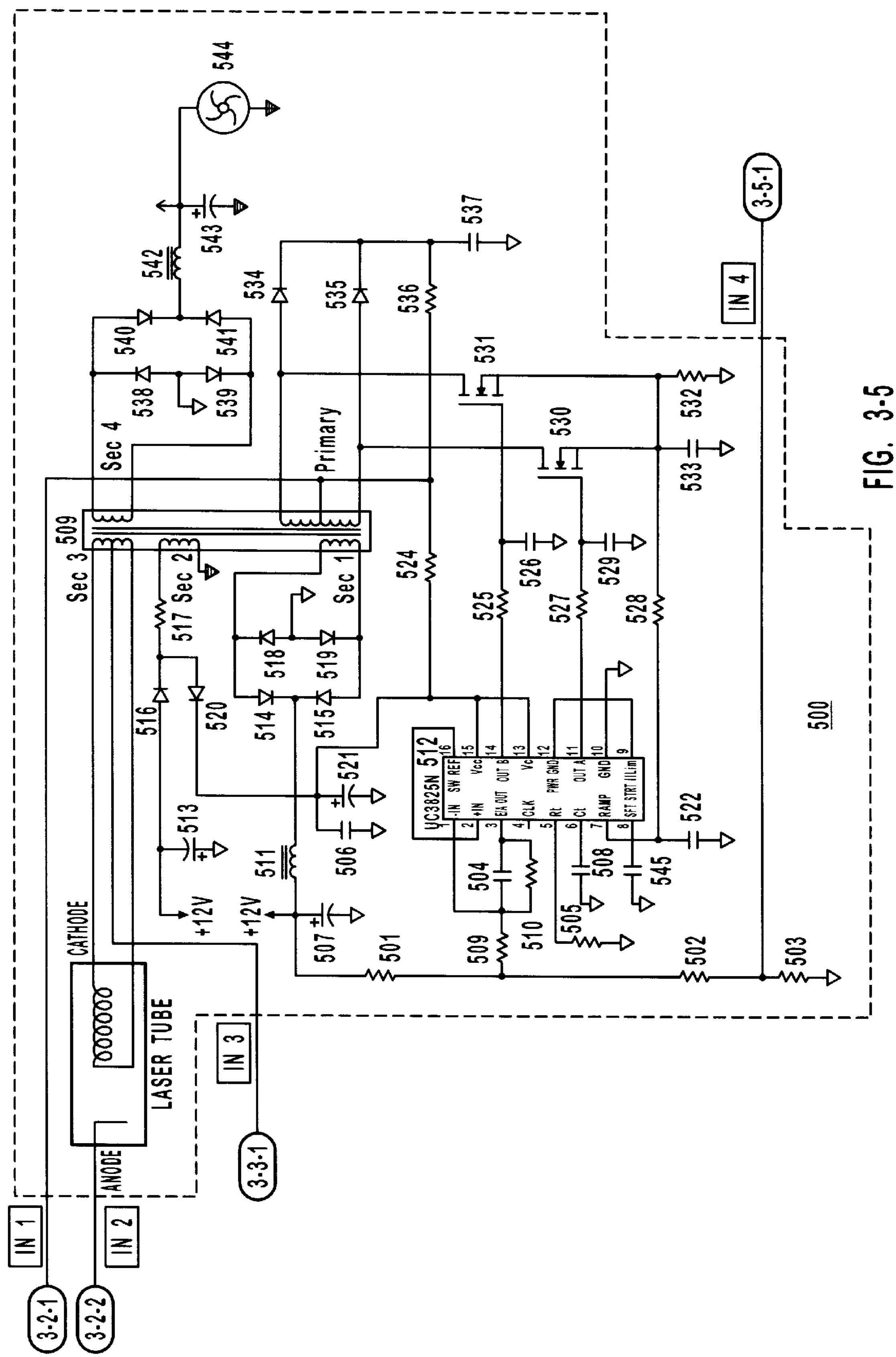
Figures 3, 4, 5, 6:
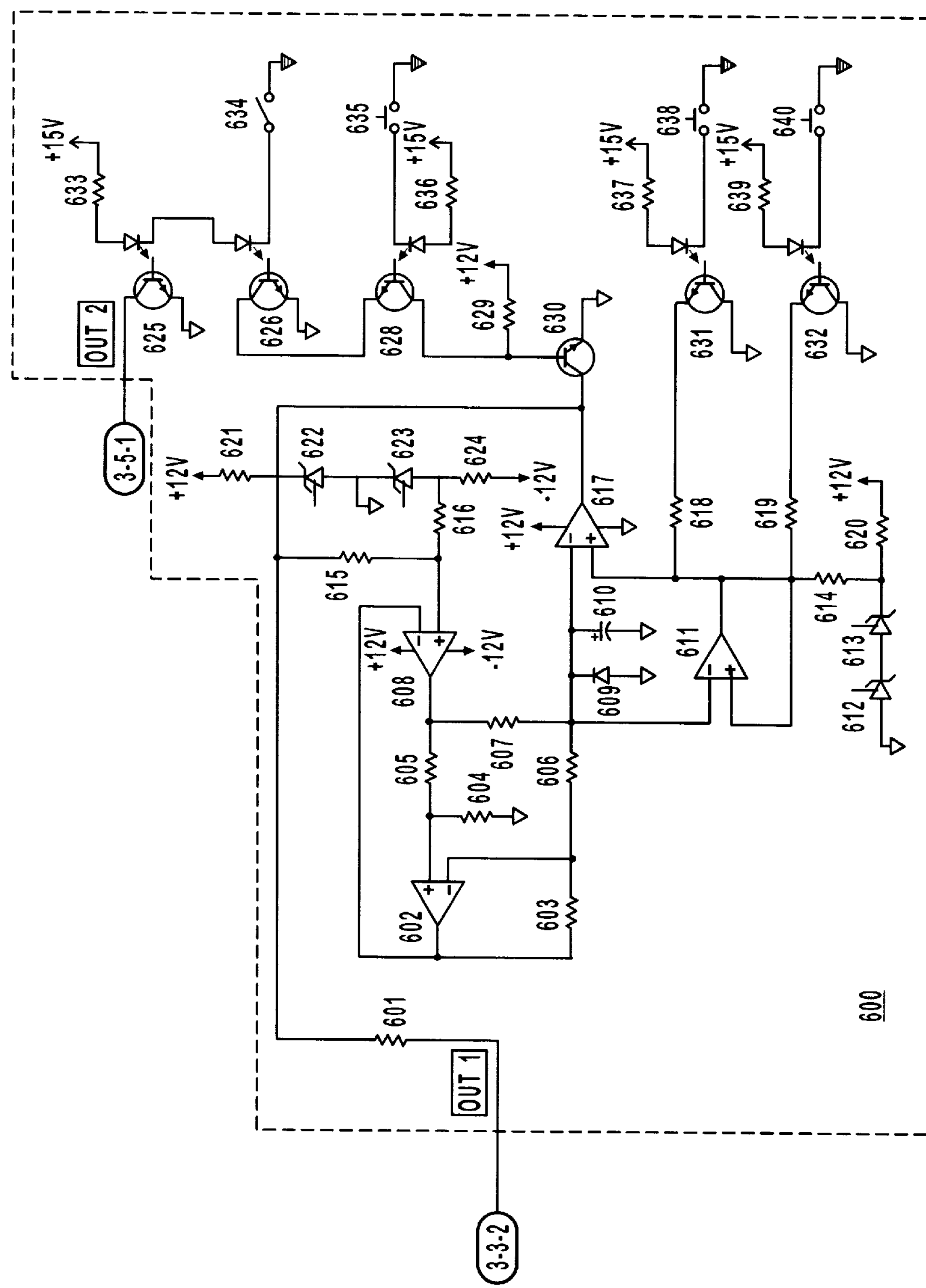
Figure 3A:
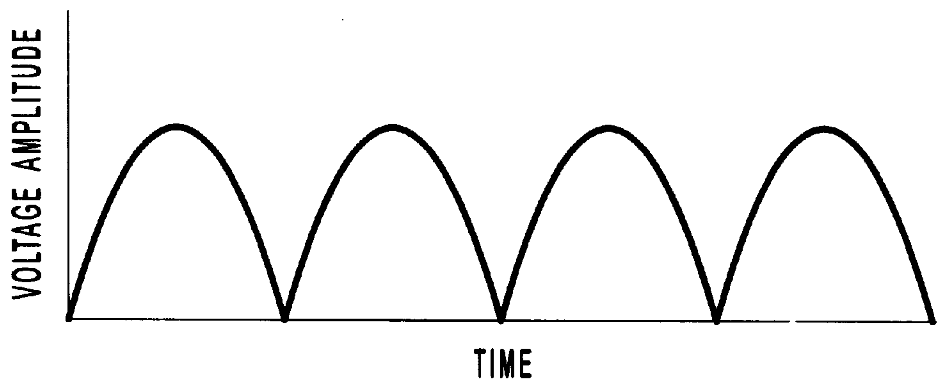
FIGS. 3A–3F depict various power and timing features of one preferred embodiment of the invention.

The purpose of the capacitor bank charge limit circuit 100 is to limit the voltage applied to capacitor 119, such that the current delivered to the laser tube is consistent. In the capacitor bank charge limit circuit 100, conditioned AC Line Voltage, present between "IN 1" and "IN 2", is applied across the AC inputs of bridge rectifier "101". The waveform of the rectified voltage between the "+" output, of bridge rectifier "101", and GND is shown in FIG. 3A, in contrast to the sinusoidal waveform that would be present if the voltage were not rectified. This same voltage waveform is also present between the cathodes of diodes "103" and "104" and "OUT 4", and GND.

Mosfets "116", "117", and "118" act as current switches to control the current flowing into capacitor "119". When these mosfets are "ON" current flows from bridge "101" "+" output, through capacitor "119", through the mosfets, and then to bridge "101" "–" output, thus allowing capacitor "119" to charge very quickly to the voltage potential present between the outputs of bridge "101". When these mosfets are "OFF" the aforementioned current flow ceases and the voltage potential across capacitor "119" then remains at the voltage potential which was present between the outputs of bridge "101" at the time that the mosfets were turned "OFF". This voltage potential, present between "OUT 2" and "OUT 3", is utilized in driving the Laser Tube. The voltage potential across capacitors 120 and 122, at "OUT 1", is equal to the peak of the rectified AC voltage and is used by the filament power supply in Section 500 (diode 121 assures that the higher voltage present across capacitors 120 and 122 does not affect the voltage potential across capacitor 119).

Figure 3B:
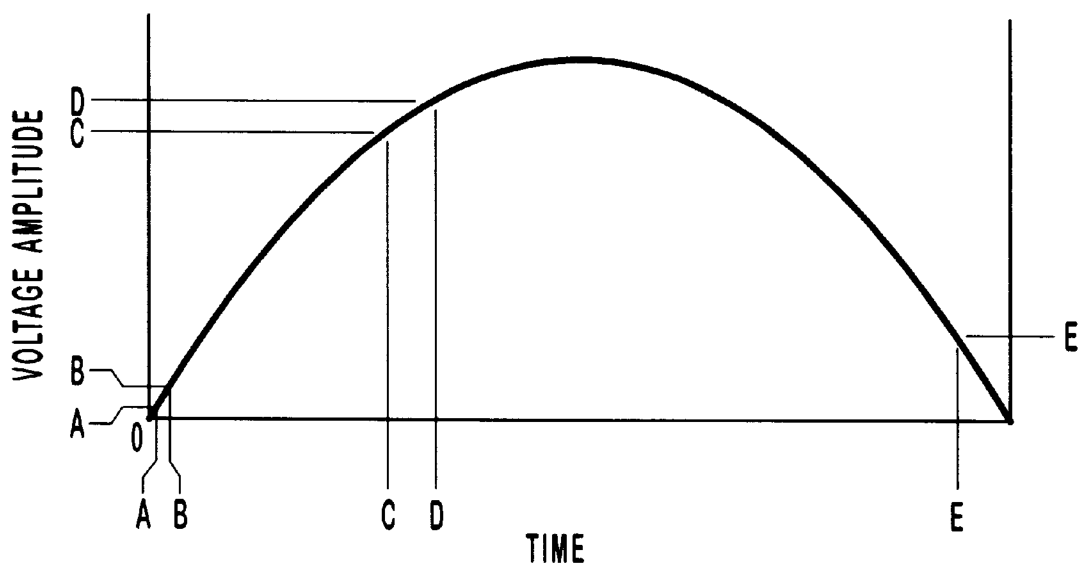

Components 102 through 115 together form a control circuit which turns mosfets 116, 117, and 118 "ON" and "OFF" at the appropriate time intervals. This circuit performs a predetermined sequence of operations during every rectified cycle (every 1/120 second). See the illustration of FIG. 3B and the sequence description below:

a. Start of new cycle (TIME=0): voltage at the cathodes of diodes 103 and 104, as measured with respect to the "–" output of bridge 101, is zero volts.

b. As the voltage at the cathodes of diodes 103 and 104 begins to rise current flows through resistor 111 to the gates of mosfets 116–118 causing the voltage at the gates of said mosfets to approximately match the rising voltage. As the voltage rises to "Voltage A" at "Time A", said mosfets begin to turn on. When the voltage has risen to "Voltage B" at "Time B", said mosfets are completely on, and zener diode 113 begins to conduct current, effectively clamping the voltage at the gates of said mosfets to the level at "Voltage B" even though the voltage at the cathodes of diodes 103 and 104 continues to rise. It should also be noted that as the voltage accross the gates of said mosfets increases, current begins to flow through resistor 110 into the base of transistor 102, thus turning on transistor 102. Hence, resistor 106 becomes bypassed.

c. Note that it must be assumed that the residual voltage across capacitor 119 was left at a voltage level equal to "Voltage C" prior to the beginning of this cycle. When the voltage at the "+" output of bridge rectifier 101 rises slightly above "Voltage C" at "Time C" current begins to flow from bridge rectifier 101 "+" output, through capacitor 119, through mosfets 116–118, and back to bridge rectifier 101 "–" output. This current flow causes the voltage across capacitor 119 to match the voltage at the "+" output of bridge rectifier 101 as the voltage continues to rise.

d. When the voltage level has reached "Voltage D" at "Time D", the voltage across resistor 105 (as determined by the resistor divider network formed by resistors 107 and 105) is high enough that current begins to flow through zener diode 108 into the base of transistor 112, thus turning transistor 112 "ON". As transistor 112 is thus turned "ON", it pulls the voltage at the gates of mosfets 116–118 to approx. 0 volts, which in turn forces said mosfets into their "OFF" states, thereby reducing the capacitor charging current, described in "C." above to near zero amps. When the voltage across the gates of mosfets 116–118 is reduced to approx. 0 volts, the current through resistor 110 into the base of transistor 102 is reduced to 0 as well. Thus transistor 102 is forced into its "OFF" state. This causes resistor 106 to become part of the voltage divider network of resistors 105 and 107, which in turn causes the effective voltage at the cathode of zener diode 108 to increase. The net result of this increase is that transistor 112 is forced to remain "ON" until the voltage at the cathodes of diodes 103 and 104 drops to "Voltage E" at "Time E", after which time the voltage at the gates of mosfets 116–118 rises to the voltage clamp level previously discussed, and said mosfets once again return to their "ON" state. There is no current flow into capacitor 119 for the remainder of the cycle, however, since the applied AC voltage at this point is below the residual voltage across capacitor 119.

Boost and Trigger Circuit 200

The purpose of the boost and trigger circuit 200 is to provide a boost voltage (between 300VDC and 500VDC in the preferred embodiment), which aids in reliable tube starting, and to provide a readily repeatable trigger circuit. The switching supply of the boost and trigger circuit 200 operates as follows.

The heart of the boost and trigger circuit "200" is a current mode "Boost" flyback topology type switching supply. Its primary components include; current mode controller IC 207, switching mosfet 214, flyback transformer 217, boost capacitor 219, trigger capacitor 222, and flyback diodes 220 and 224. The basic operation cycle of this circuit is as follows:

Pin 6 of controller IC 207 quickly rises to approx. 12V. This forces mosfet 214 into its "ON" state. With mosfet 214 in this "ON" state, current begins to flow from "+Vcc" through the primary of flyback transformer 217, through mosfet 214, and then through current sense resistor 216 to GND. During this time a large voltage (equal to the turns ratio of the transformer multiplied by "+Vcc") appears across the transformer secondary. However current does not flow in the secondary due to the blocking action of flyback diodes 220 and 224 which are reverse biased by this voltage. The current flow through the primary circuit, as defined above, continues to rise, from its initial starting value, until the current proportional voltage across current sense resistor 216 reaches a predetermined level (as determined by the error amplifier), at which point the voltage at pin 6 of controller IC 207 quickly falls to near zero volts. This forces mosfet 214 into its "OFF" state. With the mosfet in its "OFF" state, the current through the primary side of transformer 217, drops to zero. The energy, which was stored in flyback transformer 217 during the previous state now causes the voltage at the secondary of transformer 217 to switch polarity causing current to flow through diodes 220 and 224 into capacitors 219 and 222 respectively. While mosfet 214 remains in its "OFF" state, much of the energy stored in transformer 217, during the previous portion of the cycle, is transferred to capacitors 219 and 222 causing the voltage across these capacitors to rise.

This cycle repeats over and over again as specified above until the voltage at pin 2 (error amplifier negative input) of controller IC 207 reaches approximately 2.5V (note that the voltage at pin 2 is a percentage of the voltage across capacitor 222; this percentage is a function of the voltage divider network formed by resistors 204 and 205), at which time the error amplifier output voltage of IC 207 drops to near 1V which in turn causes the allowable current rise of subsequent cycles to be drastically reduced. This forces the "ON" time of each subsequent cycle to also be drastically reduced in proportion to the "OFF" time of each cycle (i.e. the Duty Cycle, or ratio of "ON" time to "OFF" time, drops to approx. 1%). Hence, the voltage across capacitors 220 and 222 will stop rising and will remain at this level until they are discharged at a future time.

Supporting components of this switching supply include resistor 202 and capacitor 203, which determine the operating frequency of this supply. Resistor 215 and capacitor 208 form a filter network to eliminate voltage spikes which may appear across current sensing resistor 216. Diodes 211 and 213, and capacitor 212 form a snubber network which limits the voltage spikes which appear at the drain of mosfet 214. Other supporting components include capacitors 201, 209 and 210, and resistor 206 which work in combination to keep critical voltages noise free.

The normal function of this power supply circuit is disabled when "IN 4" is held low (near 0V) by a circuit within Section "300".

The trigger circuit portion of the boost and trigger circuit "200" is primarily composed of capacitor 222, SCR (silicon controlled rectifier) 223 and trigger transformer 221. Other supporting components of the trigger circuit include resistors 225, 226, 229, and 230, transistor 227, and capacitor 228. The basic operation of the trigger circuit is as follows:

When "IN 4" of this section is pulled to GND by a circuit in Section "300", current flows through the base of transistor 227 through resistor 226 to GND. This forces transistor 227 into its "ON" state allowing a surge of current to flow through capacitor 228 into the gate of SCR 223. This current surge triggers SCR 223 into a conducting state. With SCR

223 in its conducting state, the voltage across capacitor 222 appears across the primary of trigger transformer 221 and then capacitor 222 is rapidly discharged through the trigger transformer primary and through SCR 223. As the voltage across capacitor 222 appears across the primary of trigger transformer 221, a very large voltage pulse appears across the secondary of this transformer; the amplitude of this voltage pulse being approx. equal to the initial voltage across capacitor 222 multiplied by the turns ratio (approx. 5KV). This large voltage pulse, which appears at "OUT 2" of this section, is enough to trigger the laser tube into conduction. When the laser tube is triggered into conduction, current begins to flow from boost capacitor 219, through the secondary of trigger transformer 221, through the laser tube, and through mosfet 340 in Section "300" to GND. This current flowing from boost capacitor 219 reduces the voltage across it until it is approx. 0.7V less than the voltage across capacitor 119 in Section "100". At this point, current begins to flow from capacitor 119, through rectifier 218, and then through the path previously described (i.e. from the capacitor bank charge limit circuit 100).

Cycle Timing Circuit 300

The purpose of the cycle timing circuit 300 is to provide the timing required to manage the 1 ms to 4 ms laser current pulse which occurs every full-wave-rectified cycle (120 times per second when operating from 60 Hz line power) used in the preferred embodiment of the invention.

This circuit provides a signal which iniates the triggering of the laser tube (at "OUT 1") at a specific time within each 120 Hz cycle, a signal which disables the switching supply of boost and trigger circuit 200 during a specific time within each 120 Hz cycle, and a circuit which turns off the tube at a specific time within each 120 Hz cycle. Each of these "specific" times is relative to the beginning of each 120 Hz cycle.

Full-wave rectified voltage as shown in FIG. 3A appears at "IN 1" and is applied across the resistor divider network formed by resistors 301 and 302 such that a percentage of the full-wave rectified voltage appears across filter capacitor 303.

Figure 3C:
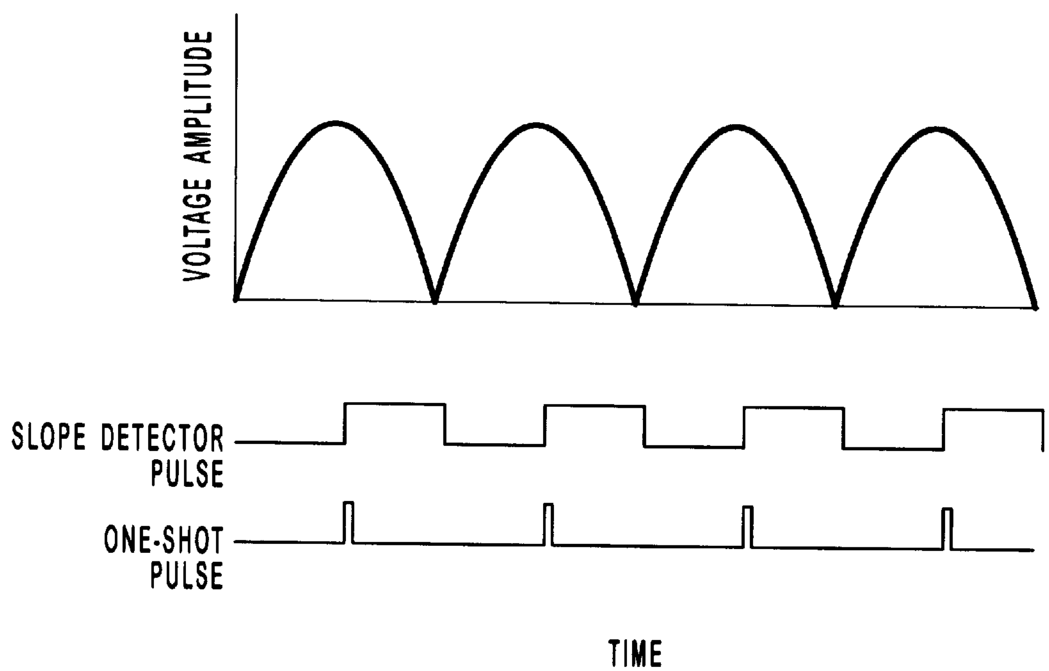

Op-Amp 307, diodes 304 and 305, and capacitor 306 together form an inverting slope detector circuit which generates a digital signal representative of the polarity of the slope of the wave-form appearing across capacitor 303. This circuit is followed by a one-shot pulse generator (composed of capacitor 311, resistors 312, 314, and 315, diode 313, and Op-Amp 316) which generates a narrow positive pulse, at the output of Op-Amp 316, that coincides with the approximate middle of each 120 Hz cycle as shown in FIG. 3C.

This one-shot pulse is used to iniate the laser trigger timer circuit during each 120 Hz cycle, and it is used to iniate the laser "Turn OFF" timer circuit during each cycle. (Note that resistor 308 and voltage references 309 and 310 provide a precision 10V reference which is utilized by both the laser trigger timer circuit and the laser "Turn OFF" timer circuit.)

Laser Trigger Timer Circuit

The laser trigger timer circuit includes comparators 322 and 325, diodes 321 and 326, potentiometer 318, resistors 317, 319, 320, and 323, and capacitor 324. At the middle of each 120 Hz cycle the one-shot pulse generator, discussed above, creates a narrow pulse at approx. 10.5 V. This pulse appears through diode 326 at the positive inputs of comparators 322 and 325 causing the outputs of these comparators to go into a high impedance state which essentially resets this timer circuit. After the timer has been thus reset, two things occur:

1. The voltage divider network, formed by resistors 317 and 319 and potentiometer 318, causes the voltage at the output of comparator 322 to be pulled up to a specific level (as determined by the setting of potentiometer 318). As soon as the one-shot pulse is gone, this voltage also appears at the positive inputs of comparators 322 and 325. In addition, the output of comparator 325 will be pulled up to approx. 12V by resistor 225 of boost and trigger circuit 200.
2. Prior to the timer being reset, the voltage across capacitor 324 was held at approx. 0.3V. After the timer reset occurs, and the output of comparator 322 goes into a high impedance state, the current flowing through resistor 320 begins to charge capacitor 324 and the voltage across capacitor 324 begins to rise. This same voltage also appears at the negative inputs of comparators 322 and 325.

Immediately after the this timer circuit has been reset by the one-shot pulse, the voltage at the positive inputs of comparators 322 and 325 is greater than the voltage at the negative inputs of these comparators. While this condition remains true the outputs of these comparators will remain in a high impedance state.

The voltage across capacitor 324 will continue to rise until it becomes slightly larger than the voltage present at the positive inputs of comparators 322 and 325 at which time the outputs of these comparators will go from a high impedance state to being drawn to approx. 0V. With the output of comparator 322 drawn to approx. 0V, current flows from capacitor 324 through diode 321 to the output of said comparator until the voltage across capacitor 324 is approx. 0.3V. Also, with the output of comparator 322 being at approx. 0V, the positive inputs of comparators 322 and 325 are also drawn to approx. OV. In this condition, with the negative inputs of comparators 322 and 325 being slight more positive (approx. 0.3V more positive) than the positive inputs of these comparators, the outputs of these comparators will remain at approx. 0V (or in other words will be latched). The timer will remain in this state until the next one-shot reset pulse.

Figure 3D:
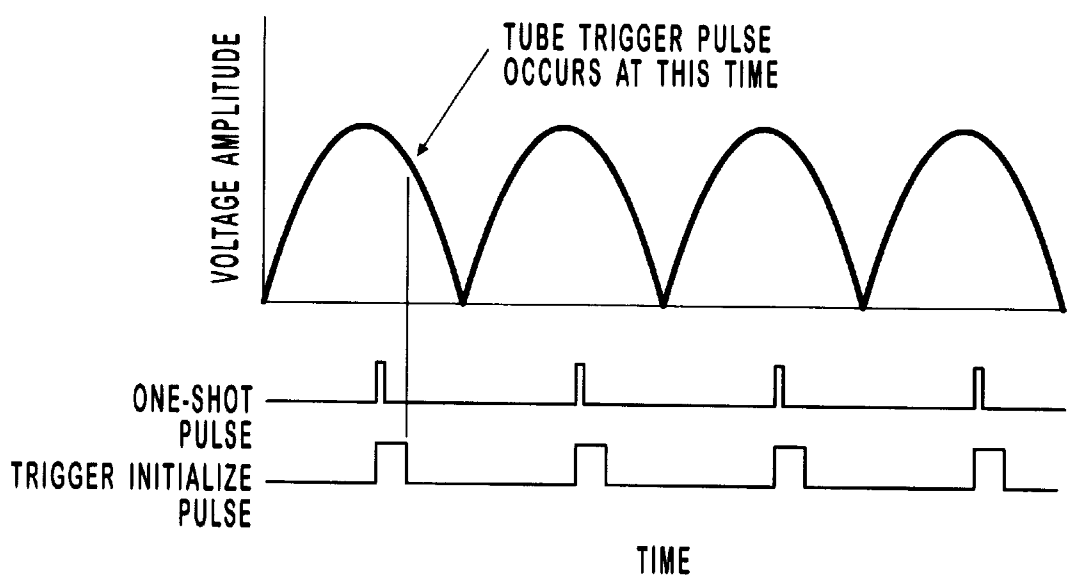

The signal at the output of comparator 325 passes through transistor 340 (if transistor 340 is turned on by the circuitry within section 600) and appears at "OUT 1" of this section and is the trigger inialize signal (i.e. when the signal at "OUT 1" goes low, the trigger circuit of Section "200" applies a trigger pulse to the tube). The timing relationship of this signal to the one-shot reset pulse is shown in FIG. 3D.

Figure 3E:
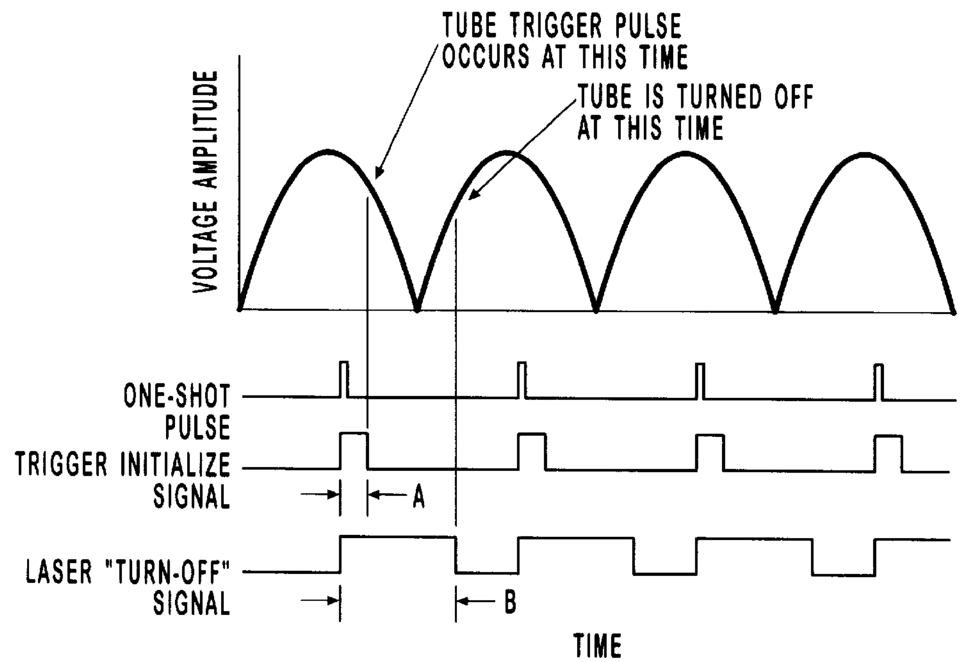

The duration of the "high" portion "A" (as shown in FIG. 3E) of the trigger initalize signal is adjustable, within limits, by adjustments made to potentiometer 318.

Laser "Turn OFF" Timer Circuit

The laser "Turn OFF" timer circuit is composed of comparators 332 and 335, diodes 331 and 336, potentiometer 328, resistors 327, 329, 330, and 333, and capacitor 334.

The laser "Turn OFF" timer circuit functions in a manner identical to the laser trigger timer circuit described above except that resistor 330 is larger in value than resistor 320, and hence the time "high" portion "B" (as shown in FIG. 3E) of the "Turn OFF" signal, although adjustable via potentiometer 328, is therefore longer than the "high" portion of the laser trigger timer signal.

When the output of comparator 335 is in a high impedance state, resistor 341 pulls this output, and capacitor 342, up to approx. 10V. This 10V is applied to the gate of mosfet 340 and forces it into its "ON" state. With this mosfet in its "ON" state, tube current can readily pass through it. However, when the output of comparator 335 is drawn down to approx. OV, the gate of mosfet 340 is also pulled down to approx. 0V as well, causing mosfet 340 to be forced into its "OFF" state. When mosfet 340 is in its "OFF" state, tube current can no longer flow through it, and the tube is therefore shut off for the remainder of that 120 Hz cycle. (Note: Zener Diode 339 is placed across mosfet 340 to protect the mosfet from voltage spikes that may occur during tube "Turn Off")

The timing relationship of the laser "Turn OFF" signal to the one-shot reset pulse is shown in FIG. 3E.

Transistor 337, diode 339, and resistor 338 are arranged such that "OUT 2" is pulled down to approx. 0V while the trigger timer signal is low and the laser "Turn OFF" signal is high. This causes the switching supply of Section "200" to be disabled while the tube is lit in order to prevent the switching supply from trying to maintain the trigger voltage across capacitor 222 and the boost voltage across capacitor 219 during this time.

AC Line Conditioning Circuit 400

There are two purposes served by the AC Line Conditioning circuitry 400. First, this circuitry provides protection for the rest of the system against line transient surges which sometimes appear on the AC Mains lines. Second, this circuitry acts to attenuate the electromagnetic noise, generated by the system, which is coupled onto the AC Mains lines.

AC line main 401 and circuit breaker 402 are shown. Gas Discharge Tube 407, resistor 404, and Metal Oxide Varistors 405 and 408 work together to snub out voltage surges or spikes which appear between either mains lines and chassis GND (earth). Metal Oxide Varistor 409 snubs out voltage surges or spikes which appear between the main lines.

Capacitors 403, 406, 410, and 412 and common mode choke 411 work together to reduce the amount of electromagnetic noise which gets back on the mains lines from the system.

Conditioned AC is applied to the system at "OUT 1" and "OUT 2".

Switching Supply for Filament and System DC Power 500

The switching supply 500 supplies power for the following:

1. Non-isolated Low voltage high frequency power to drive the laser filament;
2. Isolated +15VDC to drive the tube cooling fan and for the system and foot-switch/hand-switch interlock; and
3. Non-isolated ±12VDC to power the on board system electronics.

Shortly after the mains power has been applied to the system, a small amount of current begins to flow from capacitors 120 and 122 of Section "100" through resistor 524 and into capacitors 506 and 521, causing the voltage across said capacitors to rise. When the voltage across capacitors 506 and 521 rises to approximately 9V, switching regulator IC 512 begins to function, driving mosfet 530, through resistor 527, into its "ON" state and mosfet 531, through resistor 525, into its "OFF" state for a predetermined period of time. After this predetermined period of time has expired, then Mosfets 530 and 531 are driven to opposite states for a predetermined period of time. This switching of mosfets 530 and 531 "ON" and "OFF" in an alternating sequence is repeated time after time at a rate of approximately 20 KHz (as determined by the values of resistor 505 and capacitor 508). The predetermined period of time that each mosfet is driven into its "ON" state is a function of the frequency of operation (approx. 20 KHz), the current into the loads (i.e. the filament, +15V load, and ±12V loads), and the error amplifier output of IC 512. If the current proportional voltage, across the current sense network formed by resistors 532 and 528 and capacitors 533 and 522, begins to exceed the voltage level of said error amplifier output during any given cycle, the mosfet, which is on during that particular cycle, is immediately turned off for the remainder of that cycle. This is a current mode Push-Pull type switching topology.

Figure 3F:
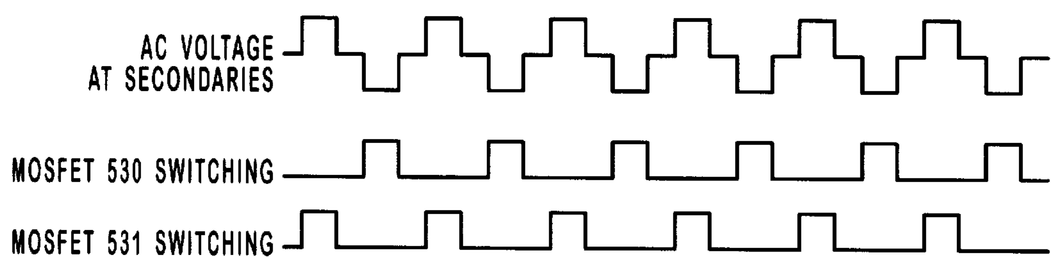
Figure 4:
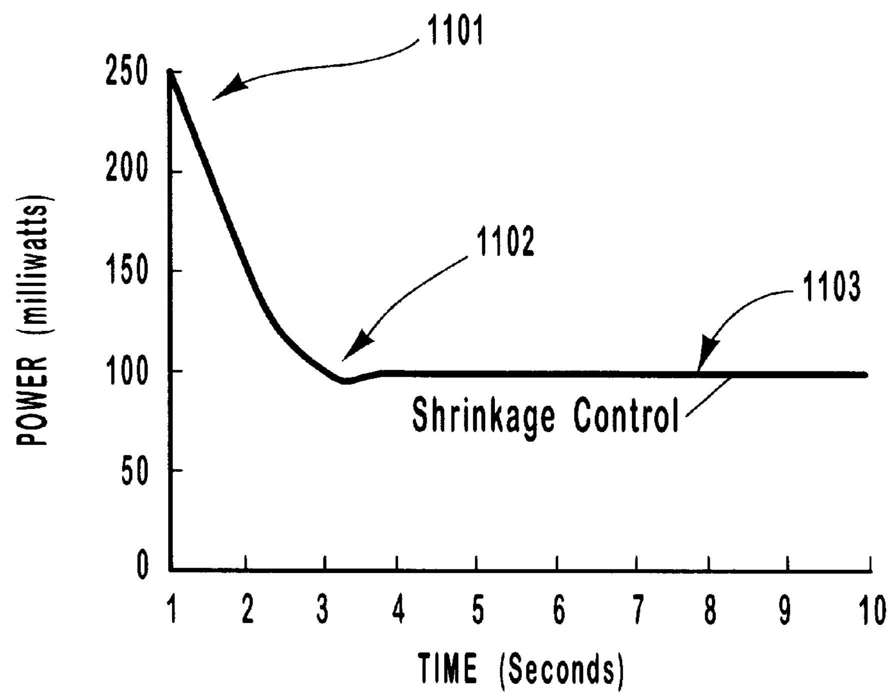
Figure 5:
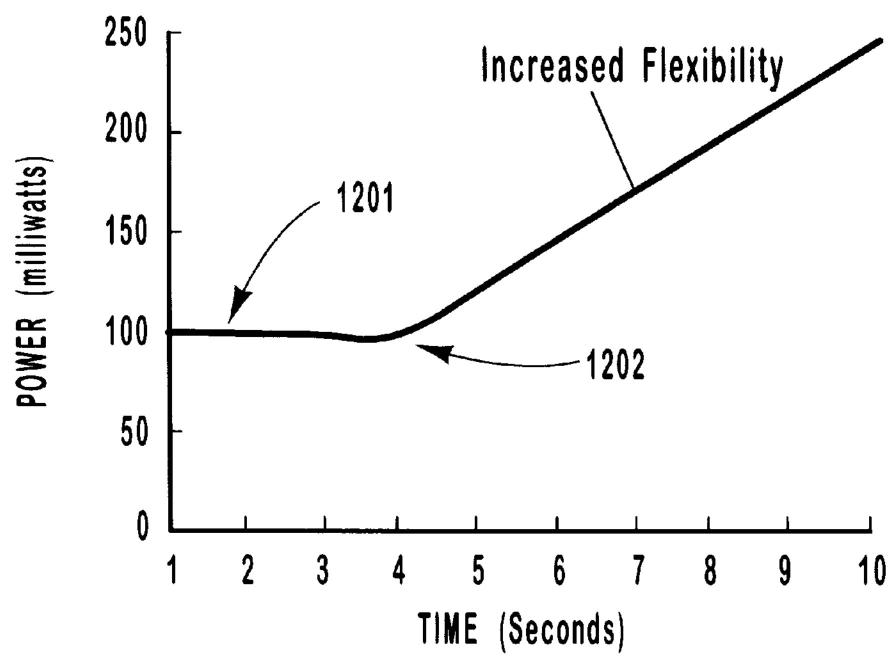
Figure 6:
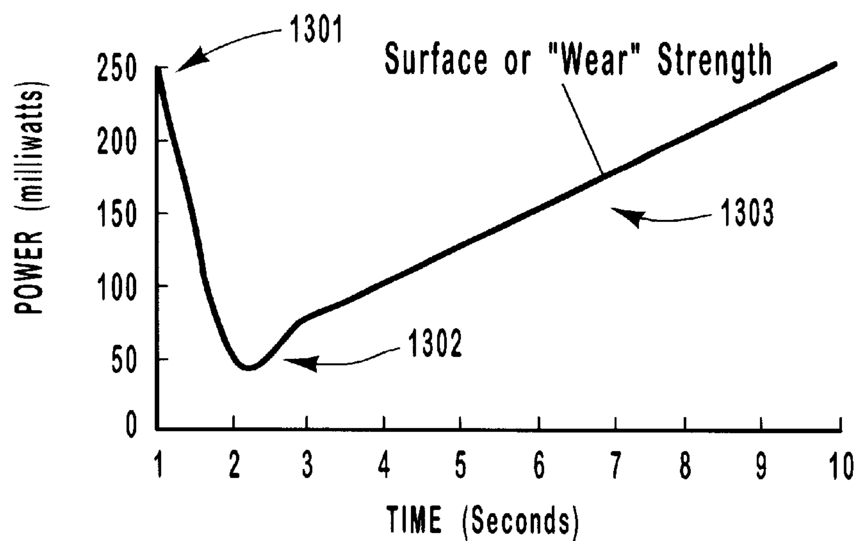

As mosfets 530 and 531 are alternately turned "ON" and "OFF", each end of the primary winding of transformer 523 is alternately pulled down to GND while the center-tap of the transformer is constantly held at the voltage level across capacitors 120 and 122 of Section 100 (approx. 150–190VDC). As the outside legs of the primary of transformer 523 are thus switched, Positive going and negative going voltage pulses are generated at the secondaries of the transformer as shown in FIG. 3F.

The amplitude of the voltage pulses at each secondary is equal to the voltage across capacitors 120 and 122 of Section "100" divided by the turns ratio of that secondary to the primary. The duration of "ON" time of each pulse, whether positive or negative going, is equal to the duration of the associated switch "ON" time.

Secondary #1

Diodes 514, 515, 518, and 519 together form a bridge rectifier which converts the AC pulse train into a DC pulse train (only positive going pulses). These positive going pulses cause current to flow through inductor 511 into capacitor 507 causing the voltage across capacitor 507 to increase. When the voltage across capacitor reaches approximately 6V, the voltage divider network formed by resistors 501, 502, and 503 will produce a voltage at pin 1 of switching regulator IC 512 will be approx. 5V (assuming that "IN 4" of this section is floating), and the switching regulator IC will then reduce the duty cycle (ratio of "ON" time to "OFF" time) such that the voltage across capacitor 507 remains at approximately 6V. (Note: When the system key switch has been turned "ON", "IN 4" will be pulled to approximately 0V. This will reduce the voltage at pin 1 of switching regulator 521 which will in turn cause the switching regulator to increase the duty cycle until the voltage across capacitor 507 rises to approx. 12V. At this point the voltage at pin 1 of switching regulator IC 512 will again be at 5V. This +12V is utilized by other system electronics.) Resistors 509 and 510 and capacitor 504 work in combination with the error amplifier portion of IC 512 to reduce the response time of said error amplifier to a suitable value.

Secondary #2

The turns ratio of secondary #2, with respect to the primary, is such that the amplitude of these high frequency AC pulses is typically 15V to 19V.

On positive polarity pulses current flows through resistor 517 and diode 520 into capacitors 506 and 521 such that the voltage across said capacitors increases from approx. 9V to approx. +13V nominally. This provides enough voltage to keep switching regulator IC 512 operational.

On negative polarity pulses current flows through resistor 517 and diode 516 into capacitor 513 such that the voltage across capacitor 513 approaches approx. −13VDC nominally. This −12V is utilized by other system electronics.

Secondary #3

The turns ratio of secondary #3, with respect to the primary, is such that the amplitude of these high frequency AC pulses is approx. 4V. These pulses are applied directly across the tube filament at the tube cathode.

Secondary #4

The turns ratio of secondary #4, with respect to the primary, is such that the amplitude of these high frequency AC pulses is approx. 20V.

Diodes 538, 539, 540, and 541 together form a bridge rectifier which converts the AC pulse train into a DC pulse train (only positive going pulses). These positive going pulses cause current to flow through inductor 542 into capacitor 543, and cooling fan 544, causing the voltage across said capacitor and fan to increase.

After AC power has been applied to the system, but prior to the key-switch being placed in the "ON" position, the voltage across capacitor 543 will increase to approx. 7.5VDC, and the fan will run at half speed. After the key-switch has been placed in the "ON" position, the voltage across capacitor 543 will increase to approx. 15VDC, and the fan will run at fall speed.

This voltage is isolated from mains lines voltage potentials for operator safety reasons. This isolation should by on the order of 4KV isolation.

Supporting circuitry includes diodes 534 and 535, resistor 536, and capacitor 537 which work together to form a snubber network to protect mosfets 530 and 531 from voltage spikes which occur during switching cycles. Other supporting components include filter capacitors 526, 529 and 545.

Interlock and Laser Treatment Timer Circuitry 600

The interlock and laser treatment timer circuitry has two purposes:

1. To provide isolated user interfaces (isolated from mains lines voltage potential) such as the key-switch interlock, foot-switch input, and 1 and 2 second laser treatment time selection inputs. 2. To provide several different laser treatment timing options such as 1, 2, and 3 second treatment times with a minimum of 1, 2, or 3 seconds of "OFF" time, respectively, between each treatment. In the preferred embodiment this is done to limit the duty cycle to a maximum of 50% so that minimal system cooling is required.

Key-Switch Interlock

After AC mains power has been applied to the system (i.e. circuit breaker 402 in the AC line conditioning circuit 400 has been engaged), the +12V rail will regulate to approx. 7.5VDC. When key-switch 634 is engaged current will flow through resistor 633, through the diode side of opto-isolator 625, through the diode side of opto-isolator 626, and then through key-switch 634 to isolated GND. This causes the transistor side of opto-isolator 625 to conduct current and hence causes "Out 2" to be pulled to GND. Shortly thereafter (approx. 50 ms later), the +12V rail will rise up to approx. 12V which then allows normal operation of all system circuitry.

Foot-switch circuitry

Opto-isolators 626 and 628, resistors 636 and 629, transistor 630, and foot-switch 635 together form the foot-switch control circuitry. After the key-switch has been engaged, current flows through the diode side of opto-isolator 626 as previously discussed. This causes the emitter of the transistor within opto-isolator 628 to be pulled to GND. This enables the rest of the foot-switch circuitry to function. When key-switch 634 is not engaged, the emitter of the transistor within opto-isloator 628 is floating, effectively disabling the rest of the foot-switch circuitry; this is a safety feature.

Prior to the foot-switch being engaged, current flows through resistor 629 into the base of transistor 630 thus causing transistor 630 to go into its conducting state. This in turn causes the collector side of transistor 630 to be pulled to GND. In this state, the laser treatment timer is held in a reset condition, and one side of resistor 601 is pulled to GND thus allowing no current flow at "Out 1" which in turn disables the trigger enable signal of Section 300.

When foot-switch 635 is engaged, current flows through resistor 636, through the diode side of opto-isolator 628, and through the foot-switch to GND. This causes the transistor side of opto-isolator 628 to go into its conducting state, and assuming that opto-isolator 628 is also in its conducting state (i.e. the key-switch is engaged), then the junction of resistor 629 and the base of transistor 630 is pulled to GND. In this condition, transistor 630 is in its non-conducting state, and the laser treatment timer circuit is enabled and the trigger enable signal of Section 300 is no longer disabled.

Laser Treatment Timer Circuitry

The laser treatment timer circuit is composed of the remainder of the components of this section. The function of this circuitry is as follows:

Timer in Reset Condition

When transistor 630 is in its conducting state (foot-switch not engaged), the junction of resistor 621, voltage reference 622, resistor 601, and the output of comparator 617 is pulled to GND (i.e. laser treatment timer held in a reset condition). In this state, the voltage divider formed by resistors 615, 616, and 624 causes a negative voltage (−1V to −2V) to appear at the positive input of Op-Amp 608. Op-Amps 608 and 602, and resistors 603, 604, 605, 606, and 607 together form a constant current source causing a constant current, proportional to, and the same polarity as, the voltage appearing at the positive input of Op-Amp 608. Thus, with a negative voltage (a portion of the negative voltage at the junction of voltage reference 623 and resistors 616 and 624) appearing at the positive input of Op-Amp 608, a voltage proportional current of negative polarity flows through resistor 607 into capacitor 610 and diode 609. This causes the voltage across capacitor 610 to fall to approx. −0.3V (with respect to GND). The voltage across capacitor 610 is prevented from going more negative by diode 609 which clamps the voltage to that level.

Timer in Active Condition

When transistor 630 is in its non-conducting state (foot-switch engaged), the junction of resistor 621, voltage reference 622, diode 601, and the output of comparator 617 is pulled up to +5VDC (as dictated by voltage reference 622). In this state, the voltage divider formed by resistors 615, 616, and 624 causes a positive voltage (+1V to +2V) to appear at the positive input of Op-Amp 608. Thus, with a positive voltage appearing at the positive input of Op-Amp 608, a voltage proportional current of positive polarity flows through resistor 607 into capacitor 610. This causes the voltage across capacitor 610 to begin to rise (with respect to GND). The voltage across capacitor 610 (which appears at the negative inputs of comparators 611 and 617) will continue to rise, at a linear rate, until it is slightly more positive than the voltage at the positive inputs of comparators 611 and 617.

The voltage at the positive inputs of comparators 611 and 617 is determined by the voltage divider networks formed by resistors 614 and 619 or 614 and 618 as follows:

a) If neither of the time selector switches, "1 second select switch" 640 or "2 second selector switch" 638, is engaged, the summation of the voltages appearing across the voltage reference circuit comprised of voltage references 612 and 613 and resistor 620—approx. 10VDC—will also appear at the positive inputs of comparators 611 and 617.

b) If "2 second selector switch" 638 is engaged, current will flow through resistor 637, through the diode side of opto-isolator 631 and then to GND thus causing the junction of resistor 648 and the cathode of the transistor within opto-isolator 631 to be pulled to GND. This causes the voltage appearing at the positive inputs of comparators 611 and 617 to be approx. 6.66V.

c) If "1 second selector switch" 640 is engaged, current will flow through resistor 639, through the diode side of opto-isolator 632 and then to GND thus causing the junction of resistor 619 and the cathode of the transistor within opto-isolator 632 to be pulled to GND. This causes the voltage appearing at the positive inputs of comparators 611 and 617 to be approx. 3.33V.

Since the voltage rise across capacitor 610 is linear, the time required to reach the three different user selectable voltage levels is directly proportional to the voltage level.) When the voltage across capacitor 610, which appears at the negative inputs of comparators 611 and 617, becomes slightly more positive than the voltage appearing at the positive inputs of these comparators, the outputs of these comparators goes from a high impedance state to being pulled to GND. With the outputs of comparators 611 and 617 at GND, all other points which electrically tie to these outputs are forced to GND as well. This causes "OUT 1" to be pulled down to approx. 0.3V thus disabling the trigger enable signal of Section "300". It also causes the voltage appearing at the positive input of Op-Amp 608 to return to a negative potential (approx. −1V to −2V) which in turn causes the constant current through resistor 607 to change polarity and in turn causes the voltage across capacitor 610 to begin to fall at a linear rate. The circuit will thus remain in this state until the voltage across capacitor 610 has fallen to a value which is slightly more negative than the voltage appearing at the positive inputs of comparators 611 and 617 (approx. 0V), at which time the cycle will begin again if the foot-switch is still engaged at that time.

Some Suggested Variations to the Preferred Embodiment

The circuitry described above is one preferred embodiment of the invention implemented by the inventors. Many variations to this preferred embodiment could be assembled, however, and the inventive concepts could be implemented in many different ways. Some such possible variations are described below.

The laser system described above, once started and stabilized, will operate between the most efficient current densities (such as between 10 and 20 amps) rather than operating continuously, like prior art lasers which are therefore inefficient. In some embodiments of the invention, a simmer or idle mode may be provided for the laser in which it would idle at a lower current, such a 5 amps. As the preferred embodiment is described above, peak output power is about 850–900 milliwatts at 20 amps. For comparison, if the same laser tube as used in the preferred embodiment were used in a continuous wave environment (rather than pulsed mode), it would generate peak output power of only 360 milliwatts. Thus, the efficiency of the invention in generating the most powerful laser output from a given laser tube can be seen. Conversely, the invention permits a desired laser output power level to be achieved using a smaller and less expensive laser tube than was available in the prior art.

When the preferred laser system is used, running the laser at 50% duty cycle provides approximately the same output results. as if the laser tube were run at 100% duty cycle in continuous wave mode. Therefore the invention permits one to build a small laser tube and run it very hard, or build a laser system with a very small laser tube running in a pulsed mode. In other words, when compared to prior art systems, the invention allows the generation of higher laser output power with a smaller laser tube.

It is known that when a laser tube is turned on or powered up, the gas in the tube tends to initially pump to one end of the tube. These laser tubes have a gas return path to allow gas to flow within the tube during use. Using the invention, it is possible to implement a laser tube with no gas return path. For each laser pulse desired, the laser tube could be turned on, gas would pump to one end of the tube, a laser output would be generated, then the laser tube could be turned off, gas would return, and the cycle could be repeated. This would allow further cost savings.

Operating a laser in pulsed mode allows the reduction or elimination of thermal load on the laser tube and thus the reduction or elimination of thermal stresses on parts of the laser system. A pulsed laser of the invention could be constructed with aluminum bores to avoid degradation and to provide sputter resistance in the bore.

The time frame in which the inventors contemplate a laser of the invention could be pulsed varies from about 1 millisecond to a continuous waveform. A continuous waveform has a cycle of about 8.3 milliseconds. The delay in the preferred embodiment from current startup to lasing is about 1.5 milliseconds.

The invention could be used to run a laser radar process looking for certain measurable differences, to initiate a camera shutter or for instrumentation. In such systems, measurements could be taken from laser pulses, and if the instruments in question were timed in sync with the laser, then they could take their timing pulses from the laser rather than attempting to time instruments and the laser separately.

The invention provides an ion gas laser that is pulsed, and the pulses are generated by the power supply. While the preferred power supply pulses every cycle of the electrical input, the power supply could pulse every other cycle, every third cycle, etc.

Another variation of the invention would be to run the laser from a first set of capacitors for one half of a waveform, then switch to another set of capacitors for the second half of a waveform, and then switch back.

In another variation of the invention, the laser can be run continuous wave to wave without extinguishing the laser. This is accomplished by recharging the capacitors every wave cycle, but providing the laser with enough energy that it can run complete wave to wave. For example, the laser may begin running at 20 amps, and continue running until it is down to 8 amps, then recharge to 20 amps.

Some additional variations of the inventive concept are as follow.

Light Feedback Embodiment

Circuitry could be implemented which would monitor a small percentage of the laser light output and then actively make real-time adjustments to the system such that the laser output remains at a user-controlled specific level. The output of this light monitor circuit could be used to adjust the laser output power in either or both of the following ways:

A. The output of the light monitor circuit could be applied to the circuitry in the capacitor bank charge limit circuit 100 such that the voltage, to which capacitor 119 is allowed to charge to, is actively adjusted to maintain a specific peak tube current per 120 Hz cycle and hence maintain a specific quantity of laser power delivered per laser pulse (120 Hz rate).

B. The output of the light monitor circuit could be applied to the circuitry in the Cycle Timing Circuit 300 such that the duration of tube current flow per 120 Hz cycle is actively adjusted to maintain a specific quantity of laser power delivered per laser pulse (120 Hz rate).

Continuous Operation Embodiment

In the preferred embodiment of the invention described above, during each 120 Hz cycle the tube is started, tube current is allowed to flow for a specific time duration, and then the tube is turned off. In an alternative embodiment of the invention that could be implemented, the tube startup could be initiated by the operator or automatically by a timer circuit. After the tube has been started (and with the tube "Turn OFF" circuitry of the cycle timing circuit 300 disabled), it could be allowed to run continuously or until the operator initiated a tube shut down. The tube start up and tube "Turn OFF" could both be initiated by the operator via the foot-switch.

This embodiment of the invention would require that additional capacitors be added in parallel to capacitor 119 in order to minimize the ripple current that each capacitor would be required to conduct. In addition, the majority of the components in the cycle timing circuit 300 could be removed (mosfet 340 and diode 339 would remain only if it were required for the operator to control the tube turn "OFF"). In this embodiment, of the invention, the majority of the components in the interlock and laser treatment timing circuitry 600 could also be removed if laser treatment timer circuitry was not required for this particular application. Only the key-switch circuitry would need to remain.

In yet another embodiment of the invention, the frequency of the laser pulses can be varied. Instead of pulsing every cycle of the 120 Hz power supply, a pulse could be generated every other cycle, ever third cycle, every fourth cycle, etc. Additionally, pulses could be sent out in intervals, such as emit 5 pulses, one pulse per cycle, then wait for a selected amount of time, then emit 10 pulses, etc.

The embodiments of the invention described above and below can produce a variable amplitude or duration pulsed laser output according to specific characteristics desired for a given application. Laser lights have many commercial, industrial and medical uses and the inventive concepts have application across all fields of laser use. One particular field of laser use which is described in detail below is the curing of dental composites.

B. General Description for Dentistry Application

The intended placement and use of a dental material affect the properties that will be desired from the material. For some dental applications, a softer and more flexible dental material is desired, and for others a harder and less flexible dental material is desired. Thus, it is important to be able to cure a polymeric dental material into a finished form with physical qualities suited for the specific function that the dental material will perform in a given patient.

In general, short polymer chains can be very hard, but they lack flexibility. Long polymer chains tend to be more flexible, but it takes them longer to form. As the longer chains form, the dental material tends to move around resulting in gaps between a tooth on which the dental materials are placed and the dental materials. The length of the polymer chains is related to how long free radical complexes can link monomers together before encountering another free radical complex. When two free radical complexes encounter each other, a bond is formed between them and the polymer-forming reaction is terminated. If this happens quickly, short chains are formed. If this happens slowly, long chains are formed. The chemical reactions being described for polymer formation are photo-initiated free radical chain reactions. A photo-initiated free radical is formed when it absorbs light energy of the appropriate wavelength. If a high amount of light energy is applied to the material, then a high number of free radicals will be formed, they will encounter and contact each other often and consequently short polymer chains are formed. If a low amount of light energy is applied to the material, few radicals will form and long polymer chains will result. The speed at which radicals in these reactions encounter each other is algebraically proportional to the concentration of the free radical formed and is described in physical chemical kinetics as the "Termination Rate". A specific example of this is diketone photo-initiated free radical polymerization which exhibits second order chemicalkinetics. This means that the Termination Rate is directly proportional to the square of the concentration of free radical initially formed by absorbing light of the appropriate wavelength. Because of this algebraic relationship small changes in the amount of light being applied can produce significant changes in how many short chain, medium length chains and long chains form as the material is curing. The specific mixture or ratio of these chain lengths govern the post-cure physical properties. By selecting the amount of light energy applied to the material, the length of chains to be formed can be selected. By adjusting or modulating the amount of light energy applied to a polymeric material at selected times during the polymerization reaction, both the length of the polymer chains and the concentration of long chains to short chains in the resulting material may be controlled. This allows the precise physical properties of the resulting material to be achieved by controlling the polymerization reaction.

There are many variables at work which influence the properties of a material after the polymerization reaction is complete. These include the polymeric material that is started with, the nature of the light, the power of the light, the duration that the light is applied to the polymeric material, modulation of the light, and others. Control of the variables is important in order to achieve the desired result.

Some of the issues that should be considered when working with polymeric dental materials include shrinkage, flexural strength and surface or wear strength. Combinations of properties addressing these issues are desired when creating pit and fissure sealants, bonding agents, and orthodontic adhesives.

For the purposes of this document, the reader should be familiar with some terms. As used herein, "polymeric" means any material that cures by converting monomers and/or their derivatives (i.e. oglimers) into polymers. Restorative dental compound means a polymeric material that is used as a direct restorative material to fill cavities or rebuild teeth. Dental material means any polymeric material that-is used in dentistry. Composite means a mixture that includes monomers and/or their derivatives (i.e. oglimers), and may also include dyes, filler materials, photo-initiator(s) and solvent(s). Cure means applying the appropriate wavelength of light to accelerate an initiator into a free radical state which, in turn converts monomers and/or their derivatives (i.e. oglimers) into polymers. Modulate means to vary intensity or power over time, such as in on/off, high/low, increase/decrease, combinations of these and other power adjustments. Dental surface means any surface of a tooth or dental appliance. This includes cutting surfaces (incisal), chewing surfaces (occlusal), vertical surfaces facing outward toward the face (facial), vertical surfaces facing inward toward the tongue (lingual), vertical surfaces facing toward the front of the head (mesial), vertical surfaces facing toward the back of the head (distal). Poly Chromatic Acusto Optic Modulator means a device that by receiving either various input frequencies or acoustical waves separates and/or mixes and/or eliminates different wavelengths of light from a multiple wavelength light source. Current Frequency or Frequency means the number of times per second the electrical current charge for a positive (+) charge to a negative (−) charge (i.e, the frequency of 60 hertz changes from positive to negative 60 times per second).

C. Direct Restorative Dental Composites

1. Shrinkage

A major concern in restorative dentistry is the shrinkage of a resin when it is cured. Once the cavity has been prepared, the composite is placed at or in the location of the tooth where tooth material had been removed and needs to be replaced. The composite is then cured. If the resin shrinks as it is cured, it will pull away from the tooth surface leaving a gap between the tooth and the resin. The gap provides a space where bacteria can leak past the restoration and cause an infection.

When curing dental material used to repair a cavity, by first applying a rapid influx of light energy (a high energy level), a matrix of short chain polymers may be set in the composite dental material very quickly. This matrix or "set" provides a rigid structure within the composite that reduces shrinkage. Once the short chain polymer matrix is formed, the amplitude of light energy can be reduced to a much lower level and held constant or otherwise adjusted. The lower level of light energy permits the remaining polymers to form long chains which can be used to provide flexibility or flexural strength in the polymerized dental material. Referring to FIG. 4, a graph is provided which illustrates one example of light power modulation with the intention of controlling or minimizing shrinkage of the dental material. The graph shows that initially light power is applied at a high level at 1101. The particular high level used in the example is 250 milliwatts. In the example, immediately upon application of the high power level it is continuously decreased to a desired point and then kept constant over time. The period of decrease in the example is about 3.5 seconds. Then the power is stabilized at a lower level 1102, such as 100 milliwatts. The lower level in the example is 40% (or less than half) of the initial power level. Power is then maintained at a constant level 1103, such as 100 milliwatts, for an additional period of time (6.5 seconds or more in the example). Note that this is approximately twice the time period of the power decrease period in the example, but could be any appropriate time period. The precise amount of time that light at high power is applied to the dental material, the way the power is reduced, the precise high and lower power levels, and the time that power is applied to the dental material are dependent both on the structural characteristics that are desired in the resulting dental material and are dependent on the composition of the dental material. In various dental materials, type and concentration of monomer, initiator, fill material and dyes vary and may require variation from the precise numbers and curve depicted in FIG. 4.

2. Flexural Strength

In certain restorations, in particular those that are on the chewing surfaces (occlusal surfaces) of the teeth, flexural strength is the post cure physical property of the dental material of most concern. For this application it is preferred that the material form the longest polymer chains possible in order to maximize flexibility. Referring to FIG. 5, a graph is depicted which indicates how it is preferred to modulate light power over time in order to maximize flexural strength of the dental material. As depicted in the graph, light power is initially kept at a constant level 1201 (such as 100 milliwatts) for a period of time (such as 4 seconds) and then progressively increased over time 1202. Note that in the example, the ending power level is about 2.5 times the initial constant power level. The precise amount of time that light is maintained at the constant power level, the way (rapidly, slowly or variably) the power is increased, the precise high and lower power levels, and the time that power is applied to the dental material are dependent both on the structural characteristics that are desired in the resulting dental material and are dependent on the composition of the dental material. In various dental materials, type and concentration of monomer, initiator, fill material and dyes vary and may require variation from the precise numbers and curve depicted in FIG. 5.

3. Surface or Wear Strength

In some dental applications such as cutting surfaces (incisal surfaces), surface or wear strength of the material is of primary concern. In such an instance, modulation of light generally like that depicted in FIG. 6 tends to maximize surface or wear strength. That includes application of instantaneous high power 1301 to produce strong short polymer chains on the surface of the dental material, reducing power over time to a low light source power level 1302 which causes long chains to form deep in the dental material, followed by increasing the light power level over time 1303 and ending at a high power level in order to finish polymerizing the dental material. The precise amount of power at various times during the curing process, the precise amount of curing time, the exact way the power is decreased and increased, the precise high and lower power levels, and the time that power is applied to the dental material are dependent both on the structural characteristics that are desired in the resulting dental material and are dependent on the composition of the dental material. In various dental materials, type and concentration of monomer, initiator, fill material and dyes vary and may require variation from the precise numbers and curve depicted in FIG. 6.

D. Pit and Fissure Sealants

Figure 7:
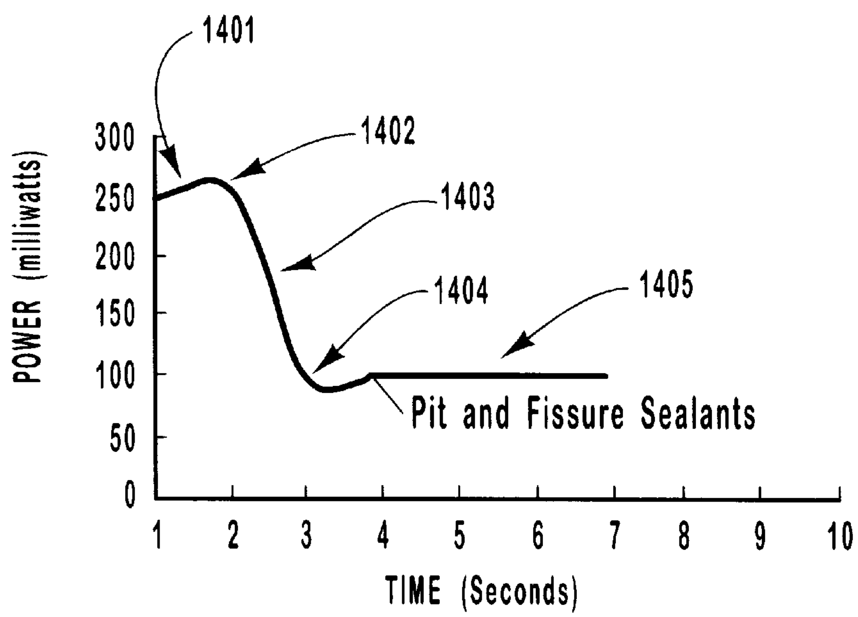

Pit and fissure sealants require strong surface or wear strength but also must shrink around the tooth for a tight fit. Referring to FIG. 7, a graph is provided which depicts light source power modulation in order to provide optimum polymerization of a dental material for use as a pit or fissure sealant. Initially light power is applied at a high level 1401 and increased some over time 1402, then rapidly dropped 1403 to a lower level 1404, increased slightly and then kept constant 1405 over time until the dental material is cured or fully polymerized. The precise amount of power at various times during the curing process, the precise amount of curing time, the exact way the power is modulated, the precise power levels, and the time that power is applied to the dental material are dependent both on the structural characteristics that are desired in the resulting dental material and are dependent on the composition of the dental material. In various dental materials, type and concentration of monomer, initiator, fill material and dyes vary and may require variation from the precise numbers and curve depicted in FIG. 7.

E. Bonding Agents for Indirect Applications

Figure 8:
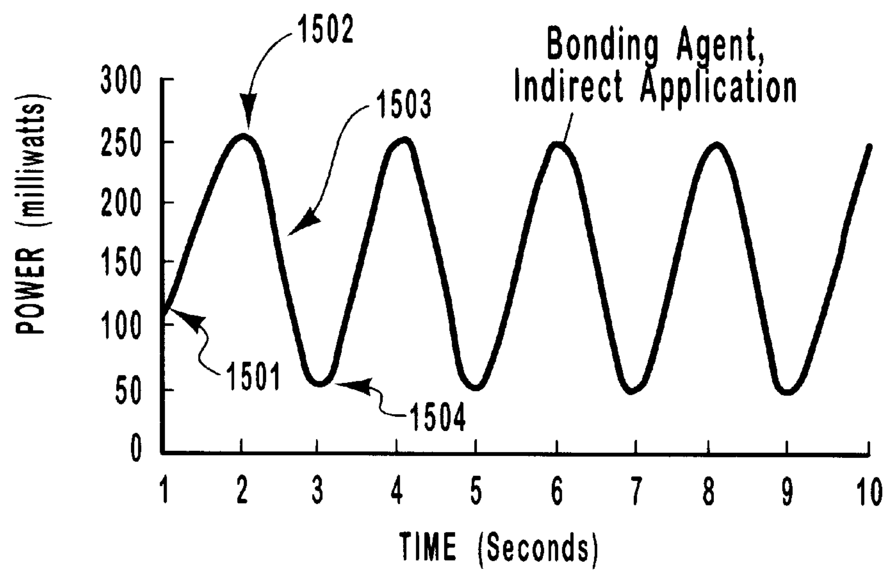

Bonding agents for indirect applications, such as crowns, bridges and veneers require maximum adhesion and flexibility, but face the unique problem that light energy must pass through the indirect restoration (crown, bridge, etc.) in order to reach the dental material to be polymerized. Referring to FIG. 8, a graph is depicted which is an example of light power source modulation requisite to penetrate the indirect restoration to start a slow polymerization reaction 1501 (e.g., 100 milliwatts), increased according to a sine function to a high power level 1502 (such as 250 milliwatts, and decreased 1503 according to a sine function to a low power level 1504 (such as 50 milliwatts), which allows the reaction to proceed and build long polymer chains. The light source power is then increased and decreased periodically according to a sine function and the cycle may be repeated more than once but perhaps many times in order to fully polymerize the dental material (i.e., in order to convert most or the majority of monomers in the dental material to polymers). The precise amount of power at various times during the curing process, the precise amount of curing time, the exact way the power is modulated, the precise power levels, and the time that power is applied to the dental material are dependent both on the structural characteristics that are desired in the resulting dental material and are dependent on the composition of the dental material. In various dental materials, type and concentration of monomer, initiator, fill material and dyes vary and may require variation from the precise numbers and curve depicted in FIG. 8.

F. Bonding Agents for Other Applications

Figure 9:
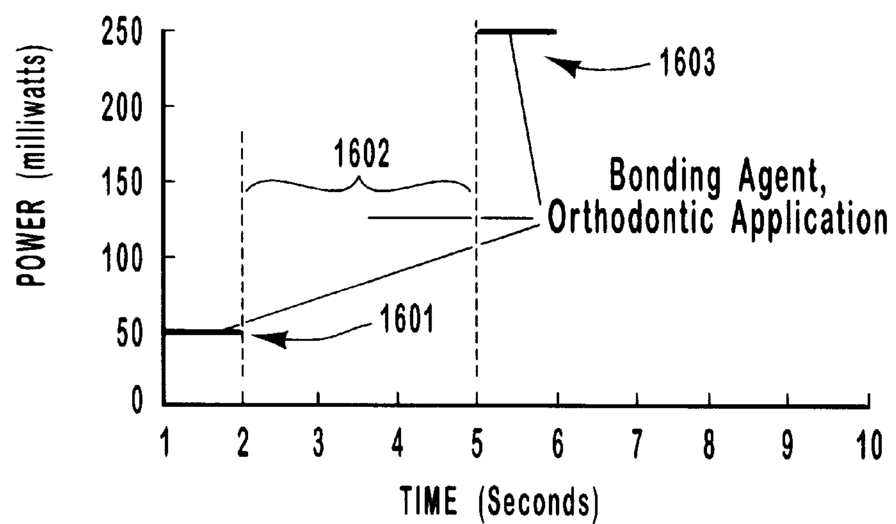

Bonding agents for other applications, such as orthodontic applications, must strongly but temporarily affix orthodontic brackets to the enamel of teeth. The dental material used for this purpose should be strong enough to withstand the rigors of orthodontic treatment but brittle enough so that when the orthodontic treatment is concluded, the dental material may be shattered or broken in order to remove the orthodontic bracket without removing enamel from the tooth. Referring to FIG. 9, a graph is depicted which shows an example of light source power modulation in order to cure a polymeric dental material to have physical characteristics desirable for bonding agents for direct applications such as orthodontic brackets. As depicted in the graph, polymerization or cure is begun 1601 with the light source at a low power for a period of time (1 second in the example). This initiates long chain polymer growth. The light source is then terminated. In the example, the light source is terminated for a time 1602. Then light is reinitiated at a high power level 603 for a brief period of time (1 second in the example) in order to cause the desired brittleness in the dental material. The discontinuous nature of the power modulation curve is believed to work best for curing dental materials for orthodontic applications.

The precise amount of power at various times during the curing process, the precise amount of curing time, the exact way the power is modulated, the precise power levels, and the total time that power is applied to the dental material are dependent both on the structural characteristics that are desired in the resulting dental material and are dependent on the composition of the dental material. In various dental materials, type and concentration of monomer, initiator, fill material and dyes vary and may require variation from the precise numbers and light source application depicted in FIG. 9.

G. Types of Dental Materials

The preferred dental material used in the various embodiments of this invention and variations of those embodiments is a polymeric dental material that includes monomer(s) (which may be of various concentrations and type), initiator(s), fill material, dyes and solvent(s). Such a dental material is polymerized by exposing it to a light source of a wavelength that causes the initiator to start and carry out polymerization of the monomers into polymers of desired lengths. The light source must be matched with the initiator so that the light source is of a wavelength that initiates and carries out the polymerization reaction.

For reference, Table I below shows various initiators (initiators) and the wavelength of light to which each is sensitive. Any of these or other initiators may be used in the invention.

TABLE I

| Initiator | Wavelength |
|---|---|
| 2-Isopropylthioxanthone | 258 nm |
| 2-tert-Butylthioxanthone | 259 nm |
| 2-Phenylthioxanthone | 267 nm |
| 2-Benzylthioxanthone | 260 nm |
| 2 Cyclohexylthioxanthone | 259 nm |
| 4-Isopropylthioxanthone | 262 nm |
| 2-Acetylthioxanthone | 255 nm |
| 2-Chloroxanthone | 240 nm |
| Fluorenone | 247 and 257 nm |
| Dibenzosuberone | 215 and 268 nm |
| 6,11-Dihydrodibenzo-thiepin-11-one | 239 nm |
| 2-Chloro-6,11-dihydrodibenzo-thiepin-11-one | 241 nm |
| Thioxanthone | 255 nm |
| 2-Chlorothioxanthone | 260 nm |
| 2-Methylthioxanthone | 258 nm |
| 2-Ethylthioxanthone | 258 nm |
| Benzoin Methyl Ether | 323 nm |
| 2,2-Dimethoxy-2-phenyl acetophenone | 335 nm |
| 2-Hydroxycyclohexane acetophenone | 320 nm |
| 1-Hydroxycyclohexane acetophenone | 326 nm |
| 2,2-Diethoxy acetophenone | 323 nm |
| Darocure-1116 | 313 nm |
| Darocure-1664 | 383 nm |
| Darocure-2273 | 383 nm |
| Thioxanthne-9-one | 378 nm |
| Camphorquinone | 467 nm |

Also for reference, in Table II below a list of various commercially-available dental materials and their source is provided.

TABLE II

| NAME | MANUFACTURER |
|---|---|
| MICROFILLED 0.04 MICRONS | |
| Durafill VS | Kulzer, Germany |
| Heliomolar | Vivadent, Liechtenstein |
| Helioprogress | Vivadent, Liechtenstein |
| Perfection | Den-Mat, Santa Maria, CA |
| Prisma Microfine | Caulk/Dentsply, Milford, DE |
| Renamel | Cosmedent, Germany |
| Silux Plus | 3M, St. Paul, MN |
| Visio Dispers | ESPE/Premier, Norristown, PA |
| SMALL PARTICLE 1–5 MICRONS | |
| Estilux | Kulzer, Germany |
| Estilux C | Kulzer, Germany |
| Paste Laminate | Den-Mat, Santa Maria, CA |
| Prisma Fill | Caulk/Dentsply, Milford, DE |
| Valux | 3M, St. Paul, MN |
| Visiofil | ESPE/Premier, Norristown, PA |
| HYBRID 0.04 + 5 MICRONS | |
| Prisma APH | Caulk/Dentsply, Milford, DE |
| Bisfil M | Bisco, Itasca, IL |
| Bisfil P | Bisco, Itasca, IL |
| Command Ultrafine | Kerr, Orange, CA |
| Conquest | Jeneric/Pentron, Wallingford, CT |
| Herculite | Kerr, Orange, CA |
| Multi-fil | Kulzer, Germany |
| P-50 | 3M, St. Paul, MN |
| Pentra-fil II | Jeneric/Pentron, Wallingford, CT |
| Pertac Hybrid | ESPE/Premier, Norristown, PA |
| Post Com II | Jeneric/Pentron, Wallingford, CT |
| Ultrabond | Den-Mat, Santa Maria, CA |

TABLE II-continued

| NAME | MANUFACTURER |
| --- | --- |
| Visarfil | Den-Mat, Santa Maria, CA |
| Visiomolar | ESPE/Premier, Norristown, PA |

I. Methods for Varying the Light Source

1. Lasers

One preferred light source for use in the invention is a monochromatic laser of a wavelength matched to the dental material. Such an arrangement limits the dental material to a single initiator that absorbs light at the wavelength produced by the laser. Multiple initiators adapted for different wavelengths may be included in the dental material and multiple light sources of appropriate wavelengths for the initiators may be employed. In some embodiments of the invention it is preferred to use a computer-controlled laser so that the exact waveform, modulation of the wave forms and power levels of light source can be produced consistently and accurately in order to achieve the desired post-cure physical properties from the composite being cured. The computer control can control the supply of electrical current to the laser and generate a variety of frequencies in different waveforms, so that as the electrical current is increased, the power output of the laser will increase, and as the electrical current is decreased the power output of the laser will correspondingly decrease mimicking the wave form and frequency generated. A light control circuit on the output side of the laser can provide exact measurement of the laser output power and feedback to the microprocessor, thereby allowing the microprocessor to deliver the pre-programmed desired power over time.

One preferred monochromatic laser for use with a single initiator (specifically camphorquinone) dental material is a 488 nanometer laser. An argon laser can be built such that it produces a very narrow band width of light around the 488 nanometer wavelength such that all photons are utilized by the initiator. The output power is monitored and adjusted according to light source power modulation techniques described herein.

The use of a single initiator in a dental material has become the standard in dentistry. The problem with single initiator dental materials is that they limit the post-cure physical properties of the dental material. The use of multiple initiators in the dental material permits the post-cure characteristics of the dental material to be more closely tailored to the desired application and is therefore preferred. Use of multiple light sources or the ability to change wavelengths one or more times during cure is necessary in order to take advantage of the presence of multiple initiators in the dental materials. Such examples would include but not be limited to multi-wavelength lasers (i.e. Krypton Ion Argon Ion mix) and mixed combinations of different lasers (i.e. and Argon Ion laser combined with an infrared diode laser in the same housing). The wavelengths of the multi-wavelength laser can be separated utilizing filters, prisms, diffraction gratings and/or Poly Chromatic Acusto Optic Modulators (also known as Acoust-Optic Tunable Filters). The preferred method would be with the Poly Chromatic Acusto Optic Modulator because it is capable of not only separating the individual wavelengths but recombining them in any percentage desired and the device is operated by applying current directly to it rather than having an electromechanical interface. An appropriate Poly Chromatic Acusto Optic Modulator can be obtained from Neos Technology, Inc., 4300-C Fortune Place, Melbourne Fla. However, any of the invented methods could be controlled (in the case of the other option listed by way of electromechanical interface such as servos and solenoids) with the same computer that controls the intensity modulation. Modulation of the intensity of the various wavelengths according to the modulation schemes described herein is also advantageous.

2. Conventional Light Sources

Although the most preferred light source used in this invention is a laser, conventional light sources (light sources other than lasers) may also be used. With non-laser light sources, however, it is difficult to produce monochromatic light. As conventional light sources produce light across a broad portion of the spectrum, it is typical to use a filter to limit the light emitted to the desired wavelength. The problem is that of producing sufficient intensities of and controlling the power of the specific wavelengths needed when there is no baseline of the percentage of power that is at the needed wavelength.

As a solution to this problem, the wavelength may be optimized by modulating input current (i.e., change the frequency of the current). When a conventional filament or short arc light bulb receives a particular frequency (i.e. 60 hertz as supplied in the US) it will produce a spectrum of light that may be more intense in the red and infrared portion of the spectrum whereas if the frequency is changed or the current is pulsed the light will produce a spectrum that is more intense in the blue wavelengths. With this understanding the utility of modifying the input current of a lamp used in curing becomes clear. Applying the current frequency that produces the greatest intensity of light in the wavelength that is needed in curing process and adding filters, prisms, diffraction gratings or other wavelength separating/eliminating devices would produce the perfect curing wavelength in much greater intensity than would otherwise be possible. It is then possible to provide an excess of the desired wavelength which can then be modulated over time to produce the post-cure physical properties desired from the material.

As an example of a dental material with more than one initiator, a two initiator dental material may be used that has a first initiator active in ultraviolet light and a second initiator active in the visible blue. The primary current to the light bulb would be modulated so that the ideal frequency for maximum ultraviolet output is achieved, the appropriate filters, prisms, diffraction gratings etc. would simultaneously be integrated into the system by the computer to eliminate the unwanted wavelengths. The microprocessor would monitor the output as described herein. The current amplitude may be increased or decreased to control the output power of ultraviolet light required. At the prescribed time the frequency of the power input would be adjusted by the microprocessor to achieve the greatest output of visible blue light, simultaneously the filter or prism or diffraction grating etc. would be changed by the computer to emit only the blue light. The amplitude of visible blue light would be measured and adjusted as already described. The use of changing the current frequency combined with conventional filtering methods provides wavelength control while simultaneously increasing/decreasing the current amplitude to modulate the intensity of the desired wavelengths produce curing control previously unavailable.

I. Examples of Light Source Power Modulation

Using the general inventive concepts outlined above, tests were performed in order to evaluate various modulation scenarios and their effectiveness for curing dental materials. The tests were designed to evaluate the effect that modulating curing light intensity over time has on the physical properties of a dental restorative material. Similar results will be expected for all areas of light-activated polymerization reaction, whether the intended field is dentistry or otherwise. In the tests performed, the restorative material was Herculite XRV available from Kerr Corporation in Orange, Calif., lot number 704675, expiration date January 2000. The samples of that dental restorative material were prepared according to ANSI/ADA Specification Number 27 (1977). Six samples were used in each test. The samples were exposed to a particular light modulation scenario utilizing an argon laser (488 nm). The diametral tensile strength was measured in accordance with ANSI/ADA Specification 27 (1977) and the mean diametral tensile strength and standard deviation were calculated. The flexibility was assessed qualitatively and confirmed by a review of the diametral tensile strength and standard deviation. In interpreting the results, the reader should be aware that more flexible samples have a lower diametral tensile strength and the standard deviation is large due to flexing before breaking.

Test #1

Figure 10:
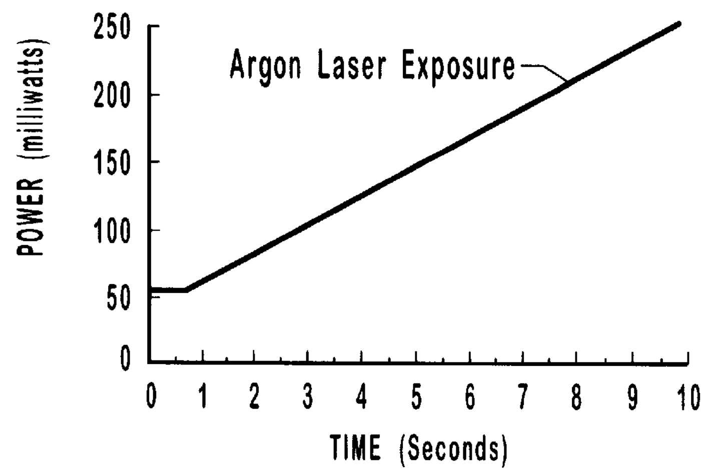

Referring to FIG. 10, it can be seen that the samples were exposed to an initially low level (50 milliwatts) of light held constant for less than a second, and the light intensity was then increased steadily over a 10 second exposure time until the curing was completed in 10 seconds at a high power level of 250 milliwatts. The results of the test were as shown in the table below. The abbreviation "Mpa" means megapascals.

| PROPERTY | RESULT |
|---|---|
| Mean Diametral Tensile Strength | 32.46 Mpa |
| Standard Deviation | 8.39 Mpa |
| Mean Diametral Shrinkage | 0.72% |

Test #2

Figure 11:
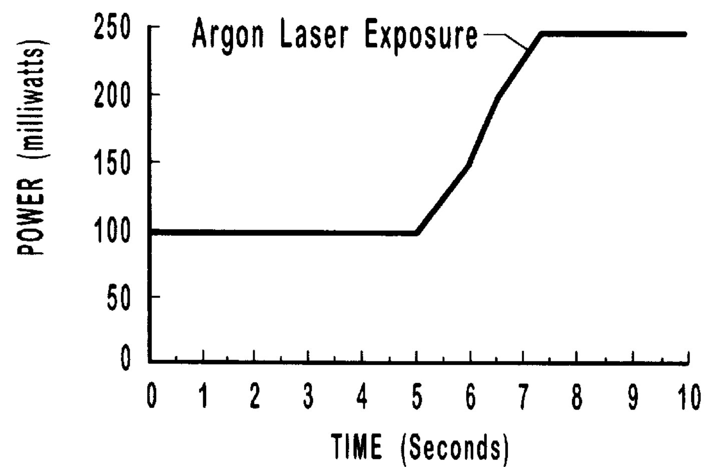

Referring to FIG. 11, it can be seen that the samples were exposed to an initially mid-level (100 milliwatts) of light held constant for five seconds, or half of the curing time. Then light intensity was increased over a 2 second period from 100 milliwatts to 250 milliwatts, and held constant at the higher power level until curing was complete. The results of the test were as shown in the table below.

| PROPERTY | RESULT |
|---|---|
| Mean Diametral Tensile Strength | 27.69 Mpa |
| Standard Deviation | 10.83 Mpa |
| Mean Diametral Shrinkage | 0.63% |

Test #3

Figure 12:
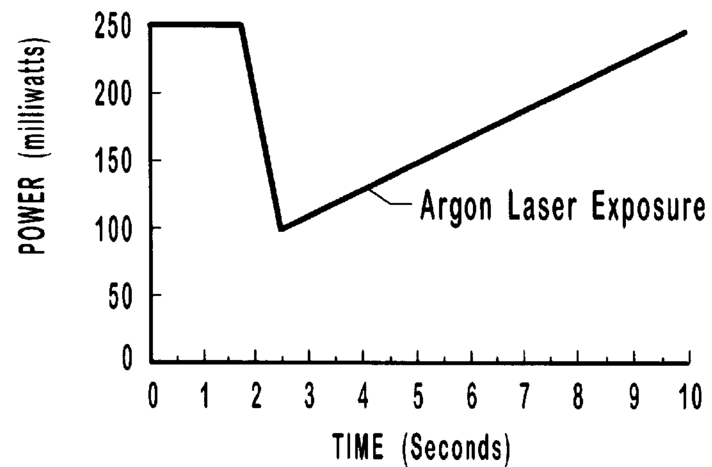

Referring to FIG. 12, it can be seen that the samples were exposed to an initially high level (250 milliwatts) of light held constant for 2 seconds. Then light intensity was abruptly decreased to a mid-level (100 milliwatts) from which it was gradually increased again to a high level (250 milliwatts) over the 10 second curing time. The results of the test were as shown in the table below.

| PROPERTY | RESULT |
|---|---|
| Mean Diametral Tensile Strength | 38.63 Mpa |
| Standard Deviation | 4.51 Mpa |
| Mean Diametral Shrinkage | 0.55% |

Test #4

Figure 13:
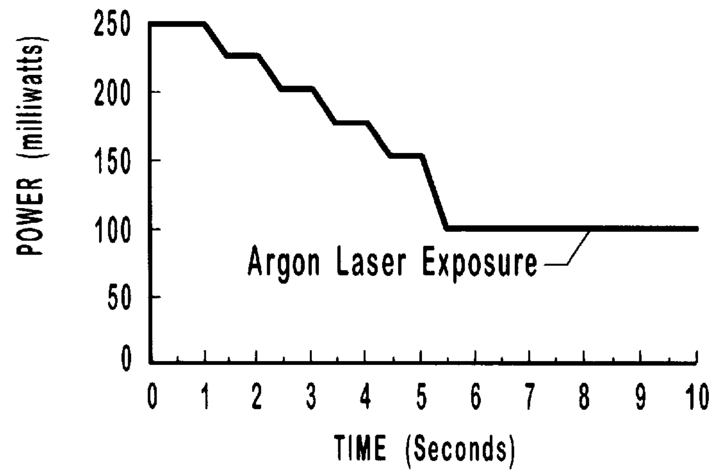

Referring to FIG. 13, it can be seen that the samples were exposed to an initially high level (250 milliwatts) of light held constant for 1 seconds. Then light intensity was incrementally stepped down about 50 milliwatts per step over 5 steps to a mid-level (100 milliwatts). At each step, the light was held constant for a brief period (about 0.5 seconds). The downward steps of light intensity were rapid but not instantaneous, as the graph shows. After 5 seconds of this gradual stepped modulation, the light level was held constant at a mid-level for the remainder of the planned curing time (in this case for an additional 5 seconds). The results of the test were as shown in the table below.

| PROPERTY | RESULT |
|---|---|
| Mean Diametral Tensile Strength | 39.55 Mpa |
| Standard Deviation | 6.47 Mpa |
| Mean Diametral Shrinkage | 0.51% |

Test #5

Figure 14:
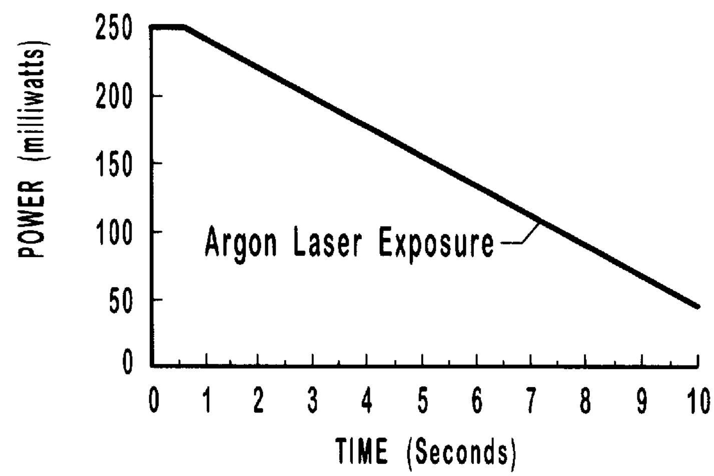

Referring to FIG. 14, it can be seen that the samples were exposed to an initially high level (250 milliwatts) of light held constant for a brief time (about 0.5 seconds). Then light intensity was gradually but continuously decreased over the remainder fo the 10 second curing time, ending at a low power level (about 50 milliwatts). The results of the test were as shown in the table below.

| PROPERTY | RESULT |
|---|---|
| Mean Diametral Tensile Strength | 34.03 Mpa |
| Standard Deviation | 5.52 Mpa |
| Mean Diametral Shrinkage | 0.49% |

Test #6

Figure 15:
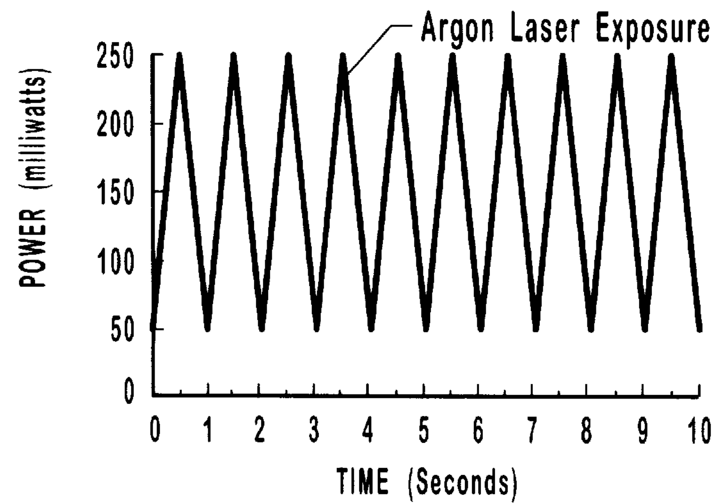

Referring to FIG. 15, it can be seen that the samples were exposed to an initial low level of light (50 milliwatts) which was rapidly increased to a high level (250 milliwatts) and decreased again to a low level (50 milliwatts) over a short time period (about 1 second). This modulation was repeated once per second over the 10 second cure time. The results of the test were as shown in the table below.

| PROPERTY | RESULT |
|---|---|
| Mean Diametral Tensile Strength | 37.37 Mpa |
| Standard Deviation | 5.20 Mpa |
| Mean Diametral Shrinkage | 0.31% |

Test #7

Figure 16:
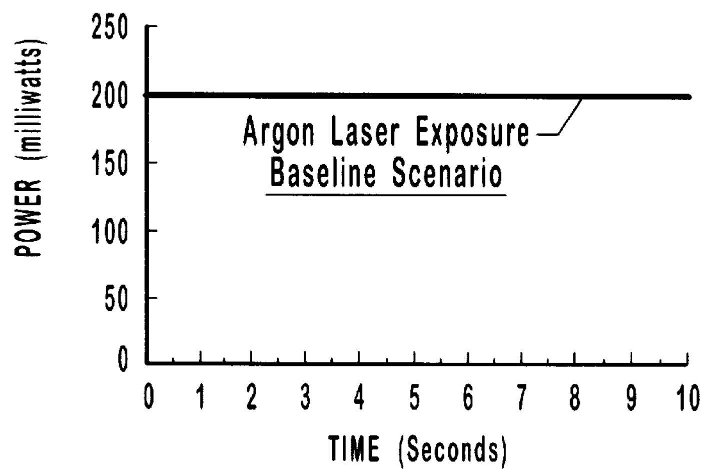

Referring to FIG. 16, it can be seen that the samples were exposed to a constant moderately high level (200 milliwatts) of light for the entire 10 second curing time. The results of the test were as shown in the table below.

| PROPERTY | RESULT |
|---|---|
| Mean Diametral Tensile Strength | 38.80 Mpa |
| Standard Deviation | 3.68 Mpa |
| Mean Diametral Shrinkage | 0.61% |

This type of curing is the current industry standard, and the post-cure properties of the dental material are typical of those achieved in the industry without use of the invention.

SUMMARY OF TEST RESULTS

Figure 17:
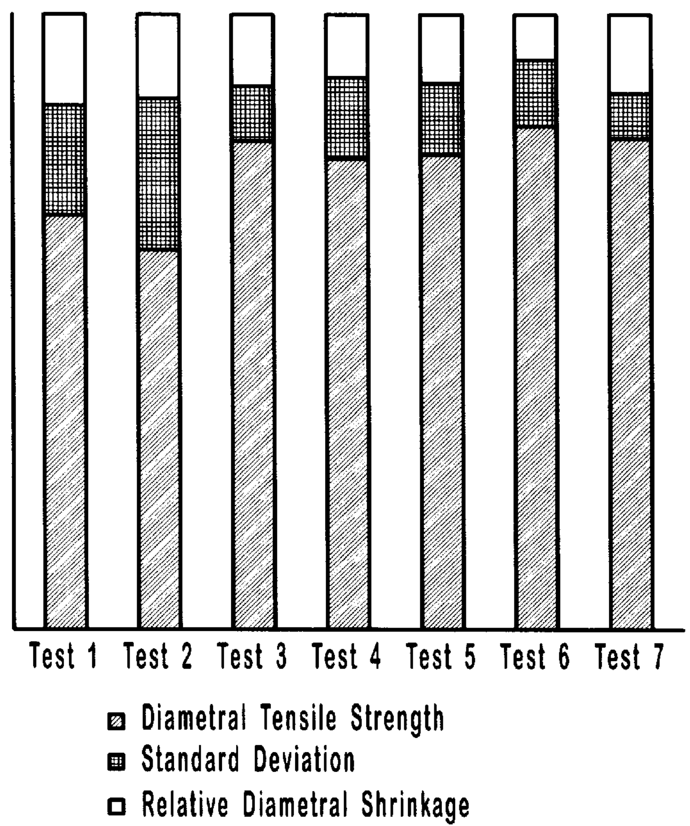
FIG. 17 depicts test results of various modulation testing using the invention.

Referring to FIG. 17, a graph is provided that compares diametral tensile strength, standard deviation and relative diametral shrinkage for each of the tests performed. Although for each test the same dental material was used as an input, the physical properties of cured dental materials from the different tests are significantly different from each other. Modulating the curing light power allows the physical properties of the resulting cured dental material to be designed and controlled. Additionally, the length of exposure of a dental material to a modulating light source will change its properties as well. Once the desired properties of the cured material for a particular application are known, power modulation and exposure times can be adjusted to produce a cured dental material meeting the desired criteria. By utilizing the invented modulation scenarios, the operator of a light source can easily decide which post-cure physical properties are desired for the particular dental application and then implement the modulation scheme which will achieve those post-cure properties. Alternatively, custom-cure modulation can be designed for unique applications.

J. Application to Various Dental Practice Scenarios

The scenarios below illustrate how a dental practitioner can implement the invention to achieve a superior cured dental material in his or her patients.

Scenario #1

If a dentist wishes to fill a large cavity on the occlusal (chewing) surface of a molar, the dentist would seek post-cure properties that include extreme hardness to avoid chipping on impact, flexibility to avoid the material fracturing under stress, and as little volumetric shrinkage as possible to avoid the potential for micro-leakage of bacteria into the tooth. For such an application, the practitioner would be best served by implementing the modulation scheme described for Test #4 above. A dental material cured by that modulation scheme exhibits excellent diametral tensile strength, good flexibility and only moderate shrinkage.

Scenario #2

If a dental practitioner wished to fill a small cavity at the junction where the tooth meets the gum line, he would want no shrinkage at all. Flexibility and hardness are not important in such a location because no force will be applied directly to the filling. Shrinkage, however, must be avoided so that the dentist will not need to perform any additional procedure to prevent micro-leakage. For such an application, the modulation scheme described for Text #6 above should be implemented.

Scenario #3

If a dental practitioner were applying orthodontic brackets, he or she would desire sufficient strength in the dental material to hold the brackets in place during orthodontic therapy, but it would be desirable to use a brittle dental material to permit shattering the dental material at the conclusion of orthodontic treatment without damage to the tooth or tooth enamel. At least 18 megapascals of tensile strength is needed for orthodontic applications. The practitioner should select either the modulation scheme of Test #3 or Test #7 for this application.

K. Industrial Applications

The invented modulation schemes and variations of them, while conceived of and tested for use in dentistry, have use wherever light-activated polymerization takes place. Below some examples of how the inventive concepts may be applied to other industries are listed.

Industrial Example #1

If an adhesive is used to bond glass and silicone to create a part for use over a broad temperature range, it is desire that the adhesive shrink to pull the glass and silicone together. But the adhesive must be flexible because glass and silicone expand and contract at different rates when exposed to heat or cold. For such an application, a polymeric composite material cured by the modulation scheme of Test #2 above is best because it provides both flexibility and shrinkage.

Industrial Example #2

If a filler material is needed to remove scratches and other production marks on a plastic cabinet before the cabinet is painted, the chosen filler should be as hard as possible to avoid future scratches and it should experience very little or no shrinkage in order to achieve the fastest finishing. For such an application, a polymeric composite cured by the modulation schemes of Tests #3 or #6 above depending on whether the particular application placed more emphasis on shrinkage or hardness.

Industrial Example #3

If a filler material is needed to restore damage to an automobile body panel, the filler should exhibit flexibility, hardness and little shrinkage. Such a balance of properties is achieved by the modulation scheme described in Test #2 above.

L. Prophetic Examples

The number of combinations of light source modulation waveforms, power levels and exposure times is infinite, and it is not possible to test more than a small subset of the possible combinations. However, a user could choose not to utilize a 10 second cure time as discussed in the tests above and instead could begin with some very short cure time and experiment with progressively longer cure times. The user could also experiment with modulating the light in intervals from a very small fraction of a second to many seconds. The user could also try mixing waveforms within a cure period. The user could utilize multiple pulses of light per second, with some or each of the multiple pulses having a different waveform.

Prophetic Example #1

Figure 18:
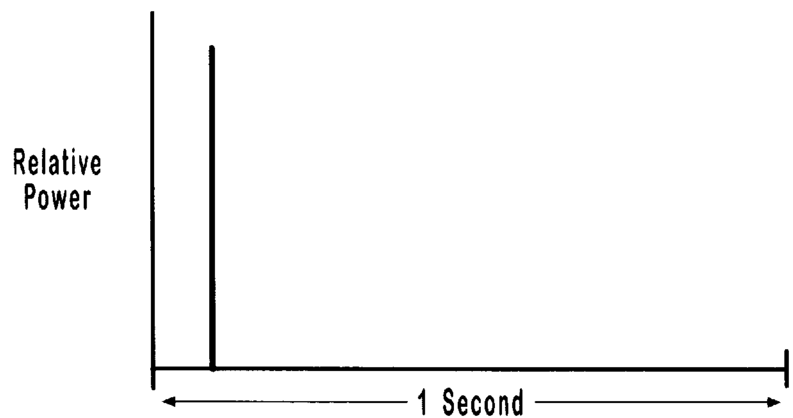
FIGS. 18–27 depict wavefoms of light sources of some embodiments of the invention.

Referring to FIG. 18, a single high intensity pulse modulation scheme is depicted. As shown, the pulse have a high level of relative power, but a very short duration, such as pico or nanoseconds.

Prophetic Example #2

Figure 19:
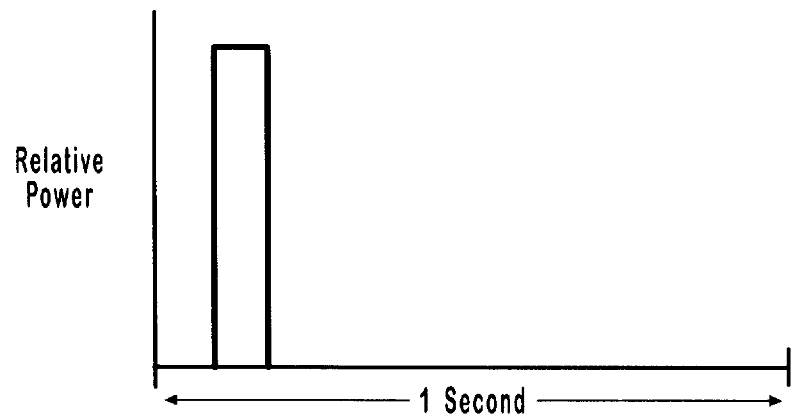

Referring to FIG. 19, a single high intensity pulse modulation scheme having a square waveform is depicted. In this example, the light source is exposed to the material to be cured at a high relative power level for a short (but not instantaneous) time period at a constant power level. The duration of the pulse can be modified to be of any desired length. Such a pulse is anticipated to be in the range of from 1 micro second or less to 0.99999+ seconds in length.

Prophetic Example #3

Figure 20:
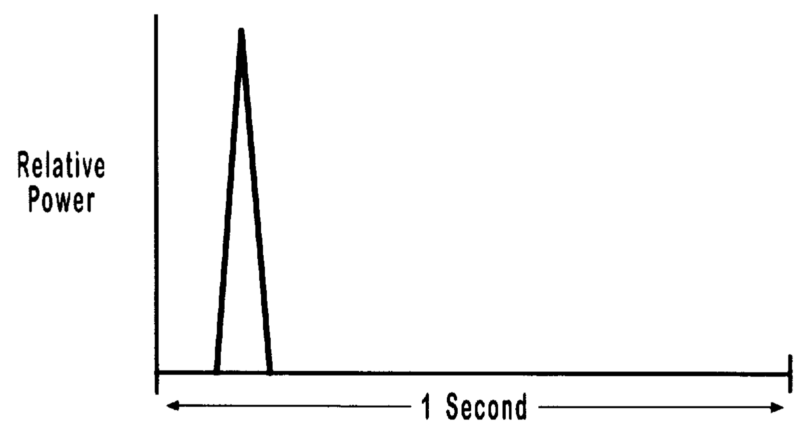

Referring to FIG. 20, a light source power modulation scheme having a triangular waveform is depicted. The duration may be modified to be shorter or longer than illustrated. The possible duration of such a waveform is from less than 1 micro second to 0.99999+ seconds in length.

Prophetic Example #4

Figure 21:
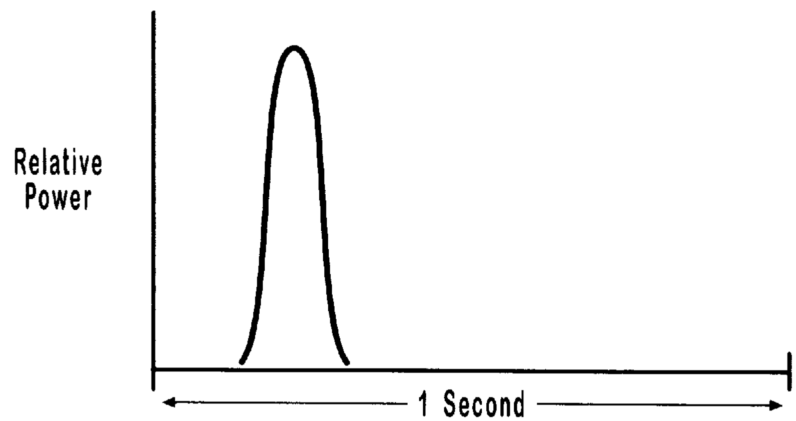

Referring to FIG. 21, a single pulse sine wave form is depicted according to which a light source for curing dental material can be modulated. The duration of a pulse of light power according to that waveform is modifiable to the desired time length, and could be from less than 1 micro second to 0.99999+ seconds in length.

Prophetic Example #5

Figure 22:
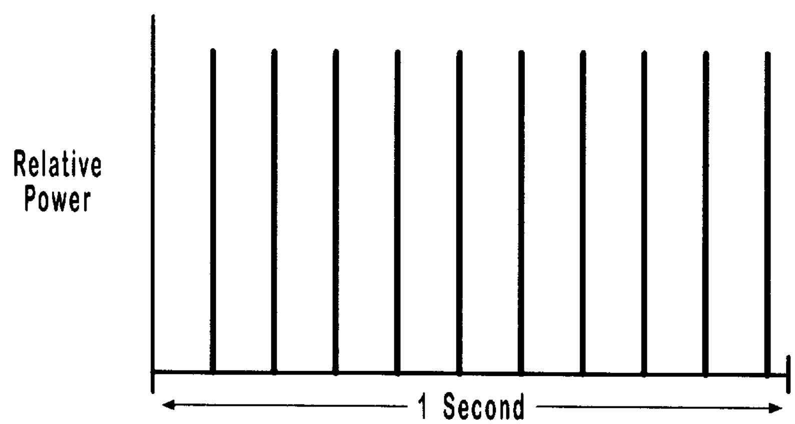

Referring to FIG. 22, a multiple pulse waveform for another modulation scheme that can be implemented according to the inventive concept is depicted. The figure depicts a single pulse of light at relatively high power in discrete intervals being repeated during a one second interval. In the figure, the pulse is repeated 10 times during a second for a frequency of 10Hz. Of course the frequency can be adjusted from 1 Hz or less to many gigahertz or more.

M. Extremely Fast Light Modulation Test

Additional testing of light source power modulation to cure dental restorative materials was performed where the intensity of the light is turned up and down many times in less than a second and carried on through the course of the entire curing time. In this testing, the restorative material used was Herculite XRV available from Kerr Corporation in Orange, Calif., lot number 704675, expiration date January 2000. The samples were prepared using ANSI/ADA Specification Number 27 (1977) and the mean diametral tensile strength and standard deviation were calculated.

Fast Modulation Test #1

Figure 23:
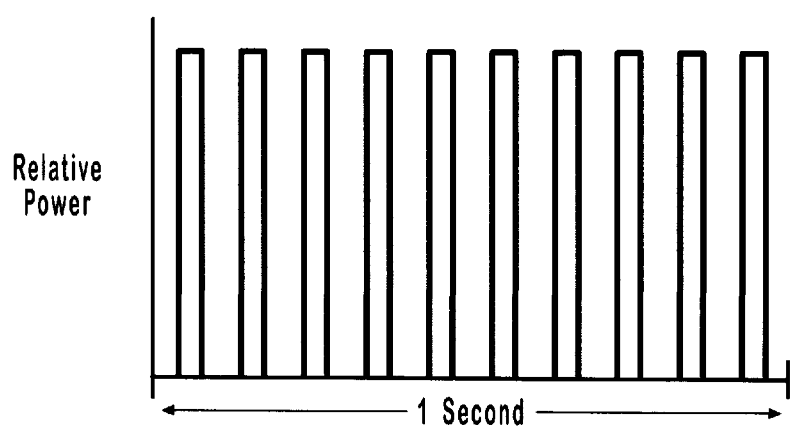

The waveform used was a square wave. The light was turned on at 250 milliwatts for 0.05 second in the square waveform, then the light was turned on for 0.05 second in a square waveform as illustrated in FIG. 23. The sequence was repeated for a total of 10 seconds The results of this test are shown in the table below.

| PROPERTY | RESULT |
|---|---|
| Mean Diametral Tensile Strength | 38.95 Mpa |
| Standard Deviation | 5.76 Mpa |

Waveform Test #2

Figure 24:
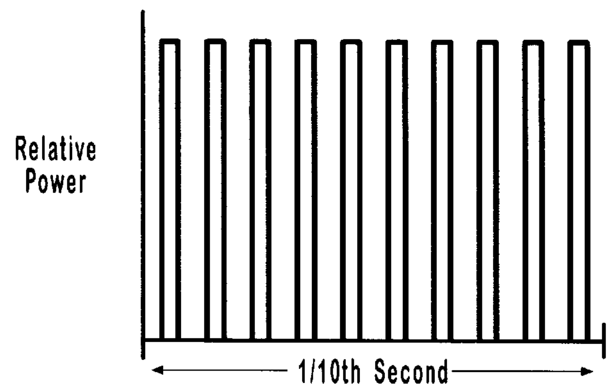

In the second test, a square waveform and 250 milliwatts of power were also used. The light was turned on for 0.005 second in the square waveform and then off for 0.005 second. The graph in FIG. 24 illustrates the waveform used. The sequence was repeated for a total of 10 seconds. The results of this test are shown in the table below.

| PROPERTY | RESULT |
|---|---|
| Mean Diametral Tensile Strength | 47.16 Mpa |
| Standard Deviation | 6.96 Mpa |

Waveform Test #3

Figure 25:
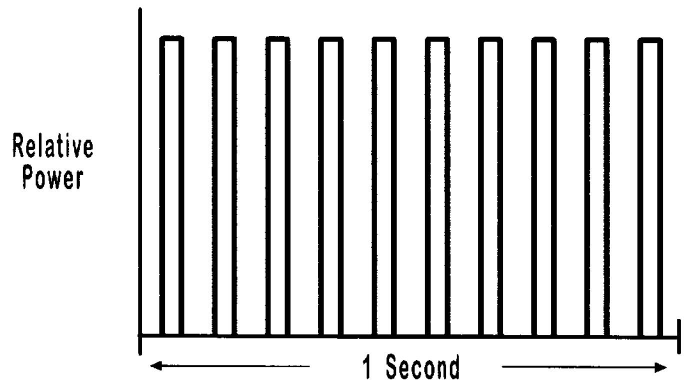

In a third test a square waveform and a 250 milliwatt power level were used. The light was turned on for 1/30th second and off for 2/30th according to the waveform illustrated in FIG. 25 (the light is off twice as long as it is on). The sequence was repeated for a total of 10 seconds. The results of this test were as shown in the table below.

| PROPERTY | RESULT |
|---|---|
| Mean Diametral Tensile Strength | 34.94 Mpa |
| Standard Deviation | 7.47 Mpa |

Waveform Test #4

Figure 26:
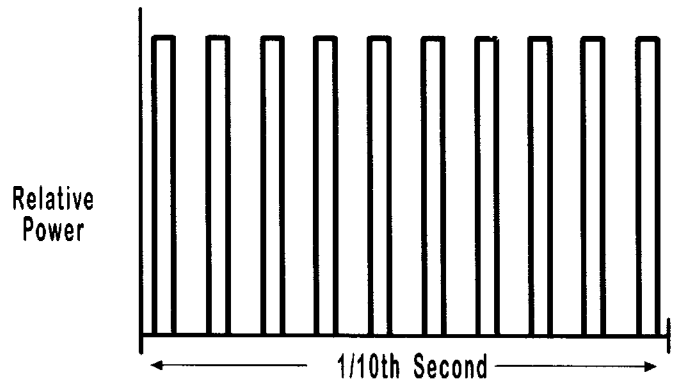

In the fourth test, a square wave form according to FIG. 26 was used with a 250 milliwatt power level. The light was turned on for 1/300th second and then turned off for 2/300th according to the waveform illustrated in FIG. 26 (the light is off twice as long as it is on). The sequence was repeated for a total of 10 seconds. The results are shown in the table below.

| PROPERTY | RESULT |
|---|---|
| Mean Diametral Tensile Strength | 40.09 Mpa |
| Standard Deviation | 3.16 Mpa |

When the results of these studies are compared, it is clear that modulating the light extremely fast (many times per second) has a profound effect on the post-cure physical properties of the material. For example, with a square wave form and 250 milliwatts of power for the same time interval, turning the light on and then off 100 times per second (on for $1/200^{th}$ and off for $1/200^{th}$) yielded a diameteral tensile strength of 47.16 Mpa but when the light was turned on and off only 10 times per second (on for $1/20^{th}$ and off for $1/20^{th}$) the diametral tensile strength was 38.95 MPa, with the difference being statistically significant. In both sets of samples the intensity of the light was 250 milliwatts, in both sets of samples the light was on for a total of 5 seconds and off for a total of 5 seconds and yet there post-cure properties were very different. The only difference between the exposure of the 2 sets is that in one set the light was turn on and off at a rate that was 10 times faster than the other.

The only difference between the first two tests and the second two tests is that the light was turned off for twice as long as it was turned on, that is to say that the light was turned on for $1/300^{th}$ of a second and then turned off for $2/300^{th}$ of a second. When considering the results of the second test, the difference in tensile strength was 40.09 MPa compared with 34.94 MPa, which approaches statistical significance. It is interesting that the samples that were turned on and off 100 times per second attained greater strength than the industry standard constant power exposure (38.8 MPa), suggesting that a beneficial result can be obtained by rest periods (periods without exposure to light) during the cure cycle. Also comparing the 10 times on and 10 times off sample to the industry standard constant power exposure, it can be seen that the 10 times on and 10 times off sample attained similar tensile strength with only 1/3 of the light exposure time. In other words the total exposure time (light on) was 3.33 seconds whereas in the industry standard the light remains on for the entire 10 seconds.

Because in the last test the light was only on for a total of 3.33 seconds and the extent of polymerization was at least as good as the current industry standard the test suggest in no small way that very discreet changes in power intensity over the course of the cure can have dramatic effects on the post-cure physical properties.

N. Summary

Figure 27:
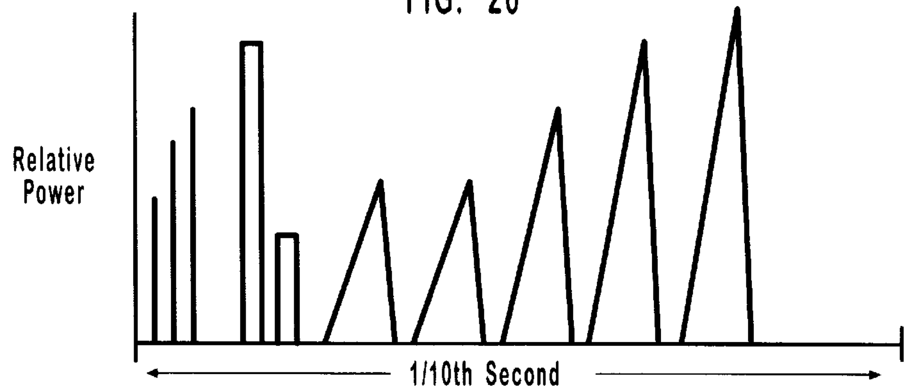

When one combines different wave forms with variable pulse widths and variable on/off rates, the possible permutations are infinite. For example, one could generate a pattern of 3 pulses, 2 square waves of 1 micro second duration and a single sine wave of 5 micro seconds duration then repeat the scenario 10 times per second. One could further modify the scenario by increasing and decreasing the power of the light source between each pulse or wave. FIG. 27 depicts an example of this type of modulation. In FIG. 27, the first of the three pulses begins at a lower relative power level and increases with each pulse. After a time without light output of any kind (a rest period), a square wave of much higher relative power is generated with a predetermined pulse width. Following the first square wave is a second square wave of lower relative power with the same pulse width. Another rest period is implemented followed by 4 triangular waves, each followed by a rest period, the first 2 being equal in magnitude and each of the succeeding 2 being of greater magnitude than its predecessor. This series could be repeated many times during cure of a material, or it could be preceded or followed by other modulation. Wave forms may be intermixed and vary in pulse width. The rest periods can be increased, decreased, placed in a different location in the series or omitted. This example is provided to illuminate possible complexity of the modulation scheme within the invention that a user may implement, anything from on single high or low intensity pulse to an infinitely complex modulation that goes on for minutes in a material that contains several initiators that require different wavelengths.

O. Equipment Discussion

Figure 28:
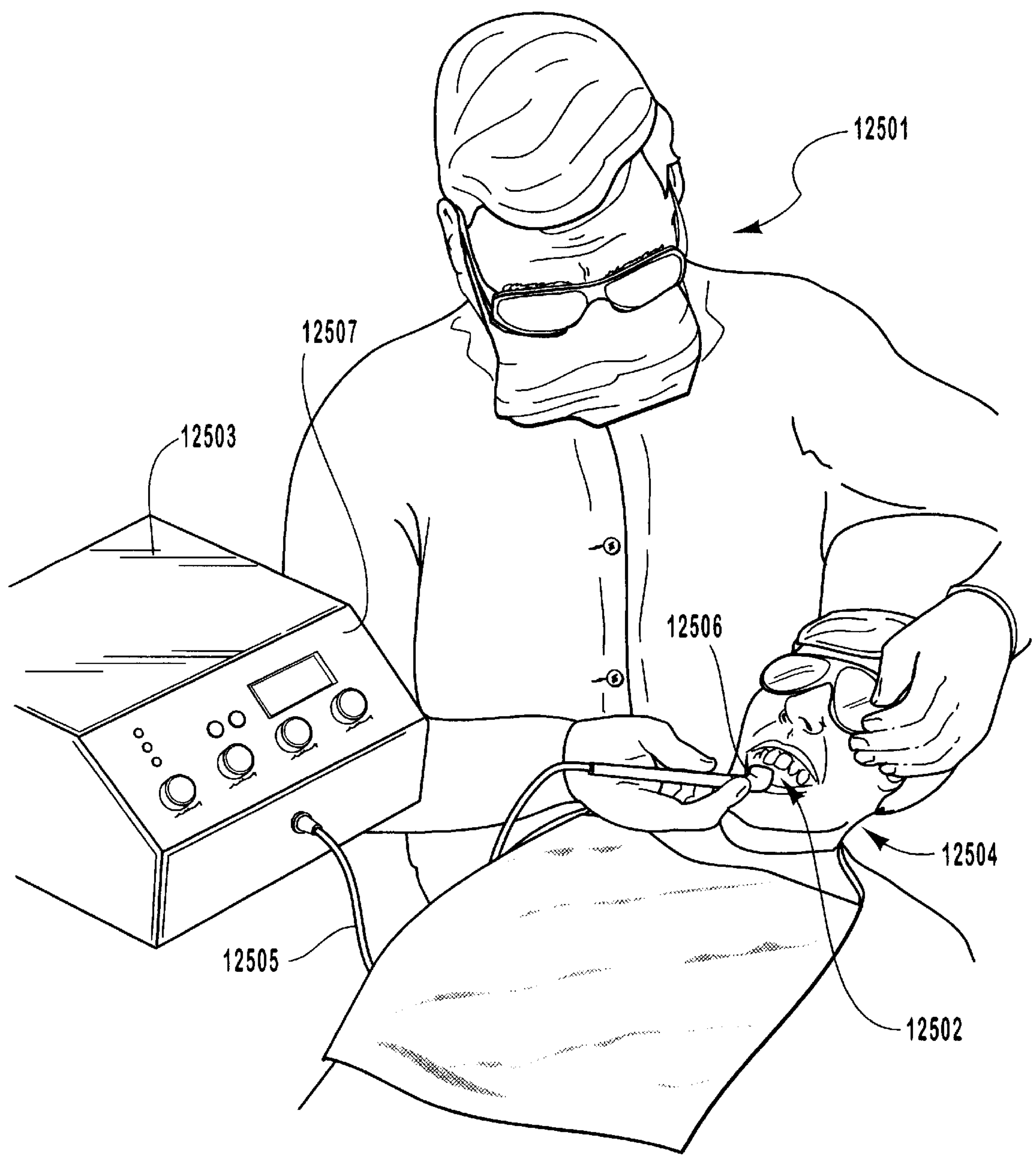
FIG. 28 depicts use of one embodiment of the invention for curing dental composites.

Referring now to FIG. 28, a representation of the invention being employed in one particular environment is provided. The figure depicts a dental office with the light source at chairside. The dentist 12501 applies the curing light 12502 that is produced by a light source 2503 to the patient 2504 by way of a light conducting device 12505 and a light delivery device 12506. The apparatus used to deliver light to the patient 12504 includes two basics parts: a fiber optic or fluid filled wave guide 12505 which is attached to the light generating source 12503 and conducts that light to the delivery handpiece 12506. The delivery handpiece 12506 preferably would have a fiber anchor system to hold the fiber securely in the handpiece, and mirrors, prisms, lens, windows or other structures to manipulate the light such that it can be delivered to the teeth in the desired manner. In this configuration, the light source 12503 within its interior includes either hardware circuitry to perform the desired modulation or a microprocessor running software that performs the desired modulation. Inputs could be accepted from a control panel on the light source 12503 in order to permit the user to select or vary the modulation scheme.

In its simplest configuration, hardware of the invention would simply incorporate an electronic circuit that would run a predetermined modulation program in a conventional dental curing light. Such a device could be shaped like a pistol, could have a rechargeable battery pack or a power cord that would plug directly into a wall outlet, could have a simple electronic circuit that turns the light up and down to predetermined intensities at a predetermined rate, could use a conventional light source, could have a narrow pass filter allowing only the desired curing wavelengths to pass and could have a glass rod that the filtered light is directed into and subsequently conducts that light to the tooth. The dentist need only plug it in, point it at the tooth and pull the trigger (i.e. push the button) that engages the automatic modulation program.

In a slightly more complex yet relatively simple configuration the invention could be rearranged such that the device and its control panel deliver electrical current rather than light to a set of electrical conductors. The conductors would then deliver the electrical current to a light source, conventional or laser, that is housed in the handpiece. In such a configuration the filters, prisms, diffraction gratings, frequency multiplying crystals, Poly Chromatic Acusto Optic Modulator or any other wavelength separating, mixing or eliminating device could be incorporated into the handpiece housing after the light source for light generation and control.

Another gross configuration of the invention would have the device that produces the light 12503 placed in a remote location in order to save space and money. In this configuration there could be several light conducting devices 12505 attached to the light producing device 12503. These light conducting devices would be long enough to go from the remote location to the dental chair where the light would be needed. With several of them attached a dentist could have a light conductor 12505, a handpiece 12506 and a control panel 12507 at each dental chair in the office. By incorporating mirrors and electo-mechanical interfaces between the actual light source and light conductor the dentist could make the appropriate command at the control panel and the light would be focused into the light conductor going to the chair where the light is needed. In this way the dentist would only need one light producing device, one central processing unit (computer control) and one set of wavelength separating/eliminating devices described herein which are the most expensive and space consuming items in the invention. They are also the most complex feature used and invention and the interaction between them is an important concept to the invention.

Figure 29:
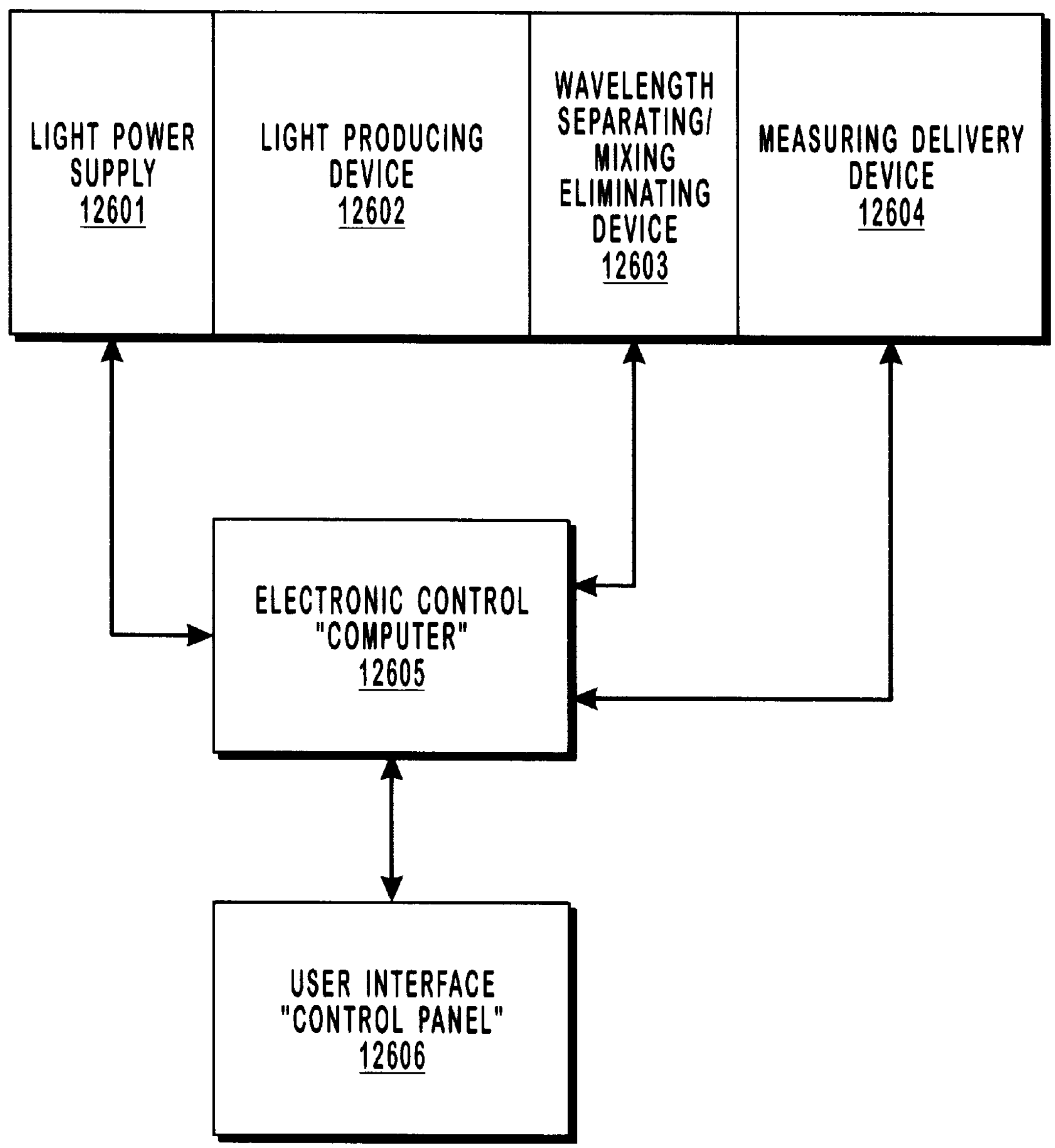
FIG. 29 is a block diagram representing hardware used in one preferred embodiment of the invention.

A component description and some interactions between them is illustrated in FIG. 29. The Light Power Supply 12601 is an electronic device that accepts power from an outside source (an electrical outlet in the dental office) and converts it into a voltage and current that can be utilized by the Light Producing Device 12602. The power supply 12601 can be as simple as a current controlling device such as a potentiometer which is simply turned up and down to increase and decrease the current and subsequently the intensity of the light being produced by the Light Producing Device 12602, or it can be extremely complicated containing current storage devices such as capacitors, frequency generators, fast switching circuits and other electronic and electrical devices that would drive the Light Producing Device 12602 to produce very rapid modulation up to tens of thousands or millions of times per second where the modulation also includes various different and complex waveforms as described herein. This complicated power supply 12601 could also simultaneously supply current of the correct frequency to maximize the production of the desired wavelength from conventional light producing devices. The Light Power Supply 12601 is controlled by interfacing with the Electronic Control 12605 (typically a microprocessor running appropriate software that implements the modulation scheme being used).

The Light Producing Device 12602 is the source for the unprocessed light. It can include a conventional light bulb such as a filament light bulb or special bulbs such as quartz halogen bulbs or bulbs filled with exotic gasses such as neon and argon or lamps such as short arc lamps and lamps filled with special gasses such as mercury vapor or sodium vapor. The Light Producing Device 12602 can included lasers such as Ion lasers, solid state lasers, diode lasers, crystal lasers, dye lasers and eximer lasers. The Light Producing Device 12602 could contain a mixture of any or all of the potential lights sources available. For instance it could include a infrared diode laser the wavelength from which could be used directly to cure the composite and then diverted to pump or excite a crystal laser the wavelength from which would then be used to further cure the initial composite or could be used to cure a different composite. An Ion laser such as argon ion and a lamp such as a mercury vapor lamp could also be incorporated into the example. In this example the configuration would include three lasers and a lamp all of which are driven or powered by the Light Power Supply 12601 which is controlled by the Electronic Control 12605.

The Wavelength Separating/Mixing/Eliminating Device 12603 receives the light from the Light Producing Device 12602 and manipulates the varies wavelengths that it receives. The device can be a simple as one narrow pass filter but may be very complex consisting of filters, prisms, diffraction gratings, frequency multiplying crystals and Poly Chromatic Acusto Optic Modulators, acusto optic tunable filters and the appropriate optical (lens, mirrors etc.) electromechanical interfaces (servos, solenoids etc.) to manipulate them. An example would be that the Light Producing Device 12602 contains an infrared diode laser that emits 810 nm, a crystal laser that produces 1064 nm when pumped with the 810 nm diode laser, an argon ion laser which produces 488 nm and a mercury vapor lamp that produces (when applied with the correct frequency) excess light in the ultraviolet region. A composite contains 4 initiators: one that absorbs at 405 m, one that absorbs at 1064 nm, one that absorbs at 488 nm, and one that absorbs at 310 nm. The composite requires a specific modulation of 405 nm for 3 seconds followed by a specific modulation of 488 nm for 5 seconds followed by a specific modulation of 1064 nm for 1 second followed by a specific modulation of 310 nm for 7 seconds and then a specific mixture of wavelengths comprised of 35 percent 488 nm, 25% 405 nm and 40% 310 nm for 4 seconds. To cure the composite the user selects the specific program and initiates the cure cycle using the user interface or control panel 12606. The Electronic Control 12605 interfaces with the Light Power Supply 12601 which fires the 810 nm diode laser and simultaneously the Electronic Control 12605 interfaces with the Wavelength Separating/Mixing/Eliminating Device 12603 causing two solenoids to rotate bringing two mirrors into alignment. The first mirror directs the 810 nm beam through a frequency doubling crystal which converts the 810 nm wavelength into 405 nm, the second mirror directs the newly created 405 nm beam into the Poly Chromatic Acusto Optic Modulator which allows the beam to pass directly into the Measuring Delivery Device 12604 (and subsequently out to the composite). After the full 3 second exposure the Electronic Control 2605 turns off the 810 nm diode laser and returns the mirrors to their original position then fires the argon laser which emits 488 nm. This beam fires directly into the Poly Chromatic Acusto Optic Modulator which allows the beam pass directly to the Measuring Delivery Device 12604 (and subsequently out to the composite). After the full 5 second exposure the Electronic Control 12605 turns off the argon ion laser and fires the 810 nm diode laser simultaneously the Electronic Control 12605 interfaces with the Wavelength Separating/Mixing/Eliminating Device 12604 causing mirrors to direct the 810 nm beam into the Nd:YAG crystal laser which produces a 1064 nm beam which fires directly into the Poly Chromatic Acusto Optic Modulator which allows the beam to pass directly to the Measuring Delivery Device 12604 (and subsequently out to the composite). After the full 1 second exposure the Electronic Control 12605 turns off the 810 nm diode lasers and returns the mirrors to their original position then fires the mercury vapor lamp the light from which is focused through a lens onto a diffraction grating. Simultaneously the Electronic Control 12605 interfaces first with the Light Power Supply 12601 instructing it to produce and send a current frequency that is ideal for ultra violet light production to the mercury vapor lamp and then with the Wavelength Separating/Mixing/Eliminating Device 12603 which rotates a solenoid attached to the diffraction grating. The diffraction grating has separated all of the wavelengths produced by the mercury vapor lamp into a rainbow band of wavelengths. The solenoid rotates the diffraction grating so that that portion of the rainbow that is rich in 310 nm wavelengths is directed into a narrow pass filter that eliminates all wavelengths except 310 nm the wavelengths then pass into a series of lens that psuedo collimate the wavelengths. The collimated light is then directed to the Poly Chromatic Acusto Optic Modulator which directly passes the light to the Measuring Delivery Device 12604 (and subsequently out to the composite). After the full 7 second exposure the Electronic Control 12605 shuts off the mercury vapor lamp and returns the diffraction grating to its original position. The Electronic Control 12605 then interfaces with the Light Power Supply 12601 and turns on the 810 nm diode laser, the argon ion laser, and the mercury vapor lamp enclosed in the Light Producing Device 12602 and it simultaneously interfaces with the Wavelength/Separating/Mixing/Eliminating Device 12603 directing it to produce 488 nm, 405 nm and 310 nm wavelengths as described above. All three of these wavelengths are passed into the Poly Chromatic Acusto Optic Modulator which receive directions from the Electronic Control 12605 to mix the relative intensity of the various wavelengths to 35% 488 nm, 25% 405 nm and 40% 310 nm. The mixture is then modulated according to the need for the prescribe remaining 4 seconds. The Electronic Control 12605 then turns off all light sources and returns all mirrors and diffraction gratings to their original position. The Poly Chromatic Acusto Modulator can not only mix a variety of wavelengths but it can also modulate different wavelengths in different modulation patterns simultaneously. When a sophisticated Light Power Supply 12601 is combined with a sophisticated Electronic Control 12605 and a Poly Chromatic Acusto Optic Modulator extremely complicated modulation patterns which includes many wavelengths simultaneously can be produced for curing composites.

The Measuring Delivery System 12604 can also incorporate a wavelength converting or eliminating feature, particularly in the delivery portion of the system. For instance the glass fiber or waveguide can directly affect the wavelengths either by being doped with material that absorbs the incident wavelength and fluoresces a new wavelength or the glass itself can be a colored fiber that filters out unwanted wavelengths or a waveguide can be used to directly filter unwanted wavelengths. An example of a doped glass fiber would be a scenario which includes a fiber made of Zblan fluoride glass that is doped with 0.5% erbium and 5.55% yttrium. When this glass fiber is struck by 980 nanometer light (a common wavelength in infrared diode lasers) it absorbs the light and produces visible blue light centered around 465 nanometers. Camphorquinone is and initiator which absorbs light preferentially, centered at 465 nanometers. Glass fibers that are doped with various fluorescing material or custom doped glass fibers are commercially available from Galileo Electro-Optics Corporation of Strubridge Mass.

An example of a glass fiber that works as a filter would be common silica glass that has specific dyes incorporated in it just as filters do. In this scenario the fiber delivery system becomes the filter as well. Fibers of this type can be custom built by Galileo Electro-Optics Corporation of Strubridge, Mass. or are commercially available from fiber optic companies such as Fiber Optic Technology, Inc. of Pomfret, Conn.

A waveguide example would be a fluid filled waveguide. Commercially available from Oriel Liquid Light Guides of Stratford, Conn. these fluid filled waveguides are very versatile in that depending on what fluid is used they only allow certain wavelengths to pass, absorbing the remaining light. For instance one might have a fluid such as water that absorbs infrared but passes or conducts most of the visible spectrum. Such a fiber would remove all of the heat generated from a short arc lamp while allowing the remaining spectrum to pass through.

The Measuring Delivery System 12604 can be as simple as a coupling mechanism for the delivery system such as a coupling for a glass fiber or fluid filled light guide. Or it can be complicated comprising beam splitters which split off a small amount of the light, photo diodes which measure that small amount of light and send a signal back to the Electronic Control 12605, shutters which open and close to stop or permit light to enter the fiber, mirrors, optics (lens) and electromechanical devices utilized when the entire device is located in a remote location to direct the light to different fibers that end up at different dental chairs.

The intent of the Measuring Delivery System 12604 is to first, in its simplest form, to provide a connection point for the light delivery system (i.e. glass fiber optic, fluid filled wave guide, glass rod etc.) and secondly to measure the light coming out of the source and communicate that information to the Electronic Control 12605. The Electronic Control 12605 then interprets the information and makes appropriate adjustments to the Light Power Supply 12601 and/or the Wavelength Separating/Mixing/Eliminating Device 12603.

The Electronic Control 12605 could be as simple as current adjustment device such as a potentiometer that is directly integrated into the Light Power Supply 12601. In this simple scenario the operator would manually turn the potentiometer up and down to predetermined intensities at a predetermined rate. Another simple configuration would be an unsophisticated electronic circuit which would automatically increase the current and/or frequency of the current automatically once initiated by the user (i.e. the user pushes a button). The Electronic Control 12605 can be extremely sophisticated having multiple interfaces to the Light Power Supply 12601, the Wavelength Separating/Mixing/Eliminating device 12603, the Measuring Delivery Device 12604 and the User Interface 12605 and incorporating very fast multi-tasking microprocessors enabling it to control all functions of the device.

The User Interface 12606 can be a simple as a button or foot switch that is engaged by the operator and as sophisticated as a computer that interfaces with the Electronic Control. In the inventions most sophisticated form the User Interface would consist of a computer key board and a computer display (i.e. CRT or LCD) and the Electronic Control would be a sophisticated computer.

Sample Software

Below some computer source code is listed which implements some of the methods of the invention. This code is considered illustrative and not in any way limiting of the scope of the invention. Persons implementing the inventive concepts could use similar or different code, instructions programmed into ROM (read only memory), a custom semiconductor chip, hard-wired circuitry, manual modulation adjustment or other techniques for carrying out the invention.

The software implements a modulation scheme by traversing a table of steps. Each step describes the power level and the duration at that level. There is a diagnostic messaging system that will give indication of the current state of the profiler test state machine. There is also a command handler that allows for dynamically setting values into the current profile for testing. The normal use is to program several profiles into the ROM and select the desired profile from the front panel menu. The execution of the selected profile is accomplished by copying the profile from ROM into RAM and then executing. This allows temporary minor changes to any ROM profile for testing.

The following is a description of the commands that are used to dynamically setup a profile in RAM for testing purposes. The ANAME command is used to identify the profile. The ASTEP command accepts three arguments: The step number, the power level, and the duration in milliseconds. The AREAD command will display the current profile settings.

```
const CMD cmd_table[ ] = {
        {"NAME",        4, CMD_name        },
        {"READ",        4, CMD_read        },
        {"STEP",        4, CMD_step        }
```

The following is the profile structure used in the software. Each profile consists of several steps each of which contain a mode selection (step/ramp [1]), a power level and a time value. The laser output is adjusted to the current power and either maintained at that level or ramped to the next step power level.

```
/*{
XXXXXXXXXXXXXXXXXXXXXXXXXXXXXXXXXXXXXXXXXXXXXXXXXXXXXXX
XXXXXXXXXXXXXXXXXXXXXX */
/*          FILE : profile.h          */
/*
************************************************************
*/
#define MAX_STEPS       20
#define MAX_PROFILES      6
typedef struct tagProfilestep
{
char mode;
int time;
int power;
```

1

```
}sProfileStep;
typedef struct tagProfile
{
int timer;
char index;                         /* current step index */
char name[17];                      /* name of profile */
sProfileStep step[MAX_STEPS];       /* steps in profile */
}sProfile;
extern void setupProfiler(void);
extern void copyProfile(char idx);
/*}
XXXXXXXXXXXXXXXXXXXXXXXXXXXXXXXXXXXXXXXXXXXXXXXXXXXXXXX
XXXXXXXXXXXXXXXXXXXXXXXX. */
```

The following code section is a test routine selected via the front panel menu. The test mode is implemented as a state machine that will setup and execute a given profile. The profile is selected via the menu sub system and execution starts when the foot switch is activated. Diagnostic messaging will report the current state of the state machine via the serial communications port.

```
case TEST_MODE:
{
 if ((HardwareStatus & keystatus) == 0) /* IF key is OFF */
 {
 reset = 1;
 ExecutiveState = STARTUP;
 break;
 }
switch (testState)
 {
 case SETUP:
 {
 putch_com('S');                        /* SETUP */
 ProfileRAM.index = 0;                  /* Initialize the index */
 operate_shutter(OPEN);                 /* Allow the shutter to open */
 testState = WAITING;                   /* Goto next state */
 putch_com('W');                        /* WAITING */
 }
case WAITING:
 {
 if ((HardwareStatus & footstatus) ! = 0) /* If foot switch is pressed */
  {
  putch_com('R');                 /* RUNNING */
  powerTime = ProfileRAM.step[ProfileRAM.index].time;
  OPERATEON                 /* Turn on the OPERATE light */
  adjust_power(ProfileRAM.step[ProfileRAM.index].power, ABSOLUTE);
  SysStat | = calflag;             /* Disable calibration */
  testState = RUNNING;             /* Goto RUN MODE */
  }
else                         /* Wait for foot switch to be pressed */
  {
  HandleModeSwitches(ROVING);     /* allow free roaming of displays */
  HandleDisplay(Display);                 /* Update Display */
  if (Display ! = TESTMODE)         /* If menu changed goto Main mode */
  {
  ExecutiveState = MAIN_OP_MODE;
  }
 }
 break;
}
case RUNNING:
{
 if ((HardwareStatus & footstatus) ! = 0) /* If foot switch is pressed */
  {
  HandleDisplay(Display);
  if (Display ! = TESTMODE)
  {
  ExecutiveState = MAIN_OP_MODE;
  }
 if (powerTime == 0)
  {
  ProfileRAM.index++;
  if ((ProfileRAM.index >= MAX_STEPS) ||
    (ProfileRAM.step[ProfileRAM.index]. time < 0))
  {
  ProfileRAM.index = 0;
  testState = PROFILEDONE;
  BUZZCOUNT(2)                       /* Beep to indicate profile done */
  putch_com('D'); /* DONE */
  }
  powerTime = ProfileRAM.step[ProfileRAM.index].time;
  adjust_power(ProfileRAM.step[ProfileRAM.index].power, ABSOLUTE);
  }
 }
else                  /* Abnormal termination of the sequence! */
 {
  clearBeeper( );               /* Reset the Beep Timer */
  BUZZCOUNT(3)      /* Beep to indicate terminated early */
  testState = PROFILEDONE;     /* Goto DONE */
  putch_com('E');              /* ERROR */
 }
 break;
 }
case PROFILEDONE:
 {
 SysStat & = ~calflag;          /* Re-enable calibration */
 HandleDisplay(Display);     /* Display the currently selected */
 HandleModeSwitches(ROVING);  /* allow free roaming of displays */
 OPERATEOFF              /* Turn off the OPERATE light     */
```

-continued

```
adjust__power(25, SET);    /* Adjust power to minimum      */
SysStat & = ~beepLong;
if((HardwareStatus & footstatus) == 0)  /* Wait for foot release */
 {
 testState = SETUP;
 }
break;
}
default:
 {
 testState = SETUP;
 }
}
break;
}
```

While complexity for its own sake is not an object of the invention, the foregoing material illustrates the ability of persons utilizing the inventive concept to tailor their modulation scheme in order to create post-cure materials having specific desired physical properties, and that the invention can be utilized for very sophisticated applications.

The foregoing provide only a few examples of the many laser output variations, pulsing, modulation schemes, power levels, light sources, frequencies, polymeric materials and curing times that could be applied using the inventive concepts. Further, only a few fields where the inventive concepts could be applied have been listed.

While the present invention has been described and illustrated in conjunction with a number of specific embodiments, those skilled in the art will appreciate that variations and modifications may be made without departing from the principles of the invention as herein illustrated, as described and claimed. The present invention may be embodied in other specific forms without departing from its spirit or essential characteristics. The described embodiments are considered in all respects to be illustrative and not restrictive. The scope of the invention is, therefore, indicated by the appended claims, rather than by the foregoing description. All changes which come within the meaning and range of equivalence of the claims are to be embraced within their scope.

What is claimed is:

1. A laser system for providing a pulsed laser output, the system comprising:

(a) a laser tube that when supplied with electrical power produces a light of a specific wavelength, (b) a laser tube output from which laser light from said laser tube is emitted, (c) a supply of electrical power for powering said laser tube, (d) control circuitry that controls said supply of electrical power so that said laser tube is powered according to a scheme that causes said laser tube to emit pulsed rather than constant laser light through said laser tube output, said control circuitry including:

(i) a capacitor bank charge limit circuit that provides consistent electrical current to said laser tube, (ii) a boost circuit which provides a boost voltage to said laser tube in order to aid in reliable laser tube starting, (iii) a trigger circuit for triggering said laser tube into a state of conduction, and (iv) a timing circuit for timing the emission of laser pulses from said laser tube, said timing circuit using a slope detector circuit to trigger a pulse generator in said trigger circuit that triggers turning on said laser tube.

2. A laser system as recited in claim 1 wherein said control circuitry further includes:

(v) circuitry for turning said laser tube off.

3. A laser system as recited in claim 1 wherein said control circuitry further includes:

(v) circuitry for isolating user interfaces from said laser.

4. A laser system as recited in claim 1 wherein said control circuitry further includes:

(v) circuitry that provides a plurality of laser pulse timing options.

5. A laser system as recited in claim 3 wherein said control circuitry permits firing said laser tube in an ON/OFF pulsed pattern such that the each period of time in which said ON period is followed by an OFF period.

6. A laser system as recited in claim 1 further comprising surge resistance circuitry to protect the laser system from power surges.

7. A laser system as recited in claim 1 further comprising noise attenuation circuitry.

8. A laser system as recited in claim 1 wherein said timing circuit provides a signal which causes said trigger circuit to trigger said laser tube at a predetermined time during a 120 Hz cycle.

9. A laser system as recited in claim 7 wherein said trigger circuit provides a trigger pulse based on a voltage waveform of said supply of electrical power and wherein said timing circuit times emission of a laser pulse from said laser tube based on a timed wait after said trigger pulse.

10. A laser system as recited in claim 9 wherein said trigger circuit generates a one shot pulse at a specfic point on a curve of full wave rectified voltage of said electrical power supply, wherein said laser tube is turned on a predetermined time after said one shot pulse, and wherein said laser tube is turned off a predetermined time after said laser tube is turned on.

11. A laser system as recited in claim 9 further comprising a timer to time turning said laser tube on and off in a pulsed manner.

12. A laser system as recited in claim 11 wherein said laser tube is turned on by said trigger timer circuit and wherein said laser tube is turned off by a timer circuit.

13. A laser system as recited in claim 1 wherein supply of electrical power has a frequency with a waveform indicating its frequency cycle, and wherein said laser emits a laser pulse once every frequency cycle.

14. A laser system as recited in claim 13 wherein said laser pulses are from about 1 millisecond to about 4 milliseconds in duration.

15. A laser system for providing a varied laser output that is an output other than a continuous laser beam, the system comprising:

(a) a laser tube capable of emitting laser light of a specific wavelength, (b) a supply of electrical power for powering said laser tube, said supply of electrical power cycling according to a predetermined frequency, (c) control means that provides controlled electrical power to said laser tube so that said laser tube emits a varied laser beam rather than a continuous laser beam, said control means including:

(i) triggering means for triggering emission of a laser beam from said laser tube, said triggering means including a pulse generator that triggers turning on said laser tube (ii) timing means for timing turning a laser beam emitted from said laser tube off, said timing means including a slope detector that initiates said pulse generator of said triggering means.

16. A system as recited in claim 15 further comprising circuitry that provides a use of the system with the ability to select from a plurality of varied laser beams to be emitted from said laser tube.

17. A system as recited in claim 15 wherein said triggering means provides a signal which causes said laser tube to emit a laser beam at a predetermined time during a power cycle.

18. A laser system as recited in claim 15 wherein said laser pulses are from about 1 millisecond to about 4 milliseconds in duration.

19. A laser system as recited in claim 15 wherein said laser beam is pulsed.

20. A laser system as recited in claim 15 wherein said laser beam is modulated.

21. A laser system as recited in claim 15 wherein said triggering means generates a one shot pulse at a specfic point on a curve of full wave rectified voltage of said electrical power supply, wherein said laser tube is turned on a predetermined time after said one shot pulse, and wherein said laser tube is turned off a predetermined time after said laser tube is turned on.

22. A laser system as recited in claim 15 further comprising circuitry that provides laser output timing options.

23. A laser system for providing a pulsed laser output, the system comprising:

(a) a laser tube that when supplied with electrical power produces a light of a specific wavelength, (b) a laser tube output from which laser light from said laser tube is emitted, (c) a supply of electrical power for powering said laser tube, (d) control circuitry that controls said supply of electrical power so that said laser tube is powered according to a scheme that causes said laser tube to emit pulsed rather than constant laser light through said laser tube output, said control circuitry including:

a capacitor bank charge limit circuit that provides consistent electrical current to said laser tube, a boost circuit which provides a boost voltage to said laser tube in order to aid in reliable laser tube starting, a pulse generator that triggers turning on said laser tube, a timing circuit for timing the emission of laser pulses from said laser tube, a slope detector circuit that initiates said pulse generator and causes emission of pulsed laser light, and circuitry for turning said laser tube off;

wherein said control circuitry permits firing said laser tube in an ON/OFF pulsed pattern such that the each period of time in which said ON period is followed by an OFF period;

wherein said timing circuit provides a signal which causes said trigger circuit to trigger said laser tube at a predetermined time during a power cycle; and wherein said trigger circuit generates a one shot pulse at a specfic point on a curve of full wave rectified voltage of said electrical power supply, wherein said laser tube is turned on a predetermined time after said one shot pulse, and wherein said laser tube is turned off a predetermined time after said laser tube is turned on.

* * * * *